(12) United States Patent
Zemel et al.

(10) Patent No.: US 9,226,790 B2
(45) Date of Patent: Jan. 5, 2016

(54) PLASMA-ASSISTED SKIN TREATMENT

(71) Applicants: Marc I. Zemel, New Rochelle, NY (US); Gennady Friedman, Richboro, PA (US)

(72) Inventors: Marc I. Zemel, New Rochelle, NY (US); Gennady Friedman, Richboro, PA (US)

(73) Assignee: M.O.E. MEDICAL DEVICES LLC, New Rochelle, NY (US)

( * ) Notice: Subject to any disclaimer, the term of this patent is extended or adjusted under 35 U.S.C. 154(b) by 0 days.

(21) Appl. No.: 13/943,012

(22) Filed: Jul. 16, 2013

(65) Prior Publication Data

US 2013/0345620 A1    Dec. 26, 2013

Related U.S. Application Data

(63) Continuation of application No. PCT/US2012/031923, filed on Apr. 2, 2012.

(60) Provisional application No. 61/584,399, filed on Jan. 9, 2012, provisional application No. 61/462,370, filed on Feb. 1, 2011.

(51) Int. Cl.
*A61B 18/04* (2006.01)
*A61B 18/08* (2006.01)
(Continued)

(52) U.S. Cl.
CPC ............... *A61B 18/042* (2013.01); *A61B 18/04* (2013.01); *A61B 18/08* (2013.01); *A61B 2018/00452* (2013.01); *A61N 5/0624* (2013.01); *A61N 5/0625* (2013.01); *A61N 2005/0662* (2013.01)

(58) Field of Classification Search
CPC ...... A61B 18/04; A61B 18/042; A61B 18/08; A61B 18/082; A61B 18/10; A61B 18/12; A61B 18/1206; A61B 18/14; A61B 18/1442; A61B 18/1445; A61B 18/1448; A61B 18/1492; A61B 2018/00452; A61N 2005/0662; A61N 5/0624; A61N 5/0625
USPC ........ 606/32–34, 41, 49; 604/20–24; 128/898
See application file for complete search history.

(56) References Cited

U.S. PATENT DOCUMENTS

| | | | |
|---|---|---|---|
| 4,672,951 | A | 6/1987 | Welch |
| 5,318,525 | A | 6/1994 | Scott et al. |

(Continued)

FOREIGN PATENT DOCUMENTS

| | | | |
|---|---|---|---|
| AU | 2006239843 A1 | 11/2006 | |
| AU | 2006279395 A1 | 2/2007 | |

(Continued)

OTHER PUBLICATIONS

European Search Report in related European application No. EP12741722, mailed Aug. 25, 2014.

(Continued)

*Primary Examiner* — Michael Peffley
*Assistant Examiner* — Khadijeh Vahdat
(74) *Attorney, Agent, or Firm* — Brian R. Pollack; Day Pitney LLP

(57) ABSTRACT

Provided are a variety of systems, techniques and machine readable programs for using plasmas to treat different skin conditions as well as other conditions, such as tumors, bacterial infections and the like. Flexible treatment electrodes are provided to conform to anatomical surfaces that can be inflatable in some implementations to conform the surface of the flexible treatment electrodes to the anatomy being treated.

25 Claims, 7 Drawing Sheets

(51) Int. Cl.
*A61B 18/00* (2006.01)
*A61N 5/06* (2006.01)

(56) References Cited

U.S. PATENT DOCUMENTS

| | | | |
|---|---|---|---|
| 5,431,649 | A | 7/1995 | Mulier et al. |
| 5,480,382 | A | 1/1996 | Hammerslag et al. |
| 6,585,718 | B2 | 7/2003 | Hayzelden et al. |
| 6,846,290 | B2* | 1/2005 | Lizzi et al. ............ 600/439 |
| 6,961,620 | B2 | 11/2005 | Rioux et al. |
| 7,850,685 | B2 | 12/2010 | Kunis et al. |
| 8,394,091 | B2 | 3/2013 | Rioux et al. |
| 8,419,681 | B2 | 4/2013 | Sell |
| 8,486,062 | B2 | 7/2013 | Belhe et al. |
| 8,535,303 | B2 | 9/2013 | Avitall et al. |
| 8,583,260 | B2 | 11/2013 | Knudson |
| 2005/0021016 | A1* | 1/2005 | Malecki et al. ............ 606/27 |
| 2005/0038375 | A1 | 2/2005 | Nitzan et al. |
| 2006/0134031 | A1 | 6/2006 | Decola et al. |
| 2006/0189976 | A1 | 8/2006 | Karni et al. |
| 2007/0239156 | A1 | 10/2007 | Palanker et al. |
| 2008/0045879 | A1 | 2/2008 | Prausnitz et al. |
| 2009/0125022 | A1* | 5/2009 | Saadat et al. ............ 606/41 |
| 2010/0145253 | A1 | 6/2010 | Gutsol et al. |
| 2011/0118719 | A1* | 5/2011 | Vissy et al. ............ 606/33 |
| 2012/0259270 | A1* | 10/2012 | Wandke et al. ............ 604/23 |
| 2013/0184702 | A1 | 7/2013 | Neal et al. |
| 2013/0261389 | A1 | 10/2013 | Long |
| 2013/0310731 | A1 | 11/2013 | Gutsol et al. |

FOREIGN PATENT DOCUMENTS

| | | |
|---|---|---|
| CA | 2605650 A1 | 11/2006 |
| CA | 2620294 A1 | 2/2007 |
| CA | 2573522 A1 | 7/2007 |
| EP | 1755733 A2 | 2/2007 |
| EP | 1810626 A2 | 7/2007 |
| EP | 1876986 A2 | 1/2008 |
| EP | 1924698 A2 | 5/2008 |
| IL | 180519 A | 2/2014 |
| JP | 10286316 A | 10/1998 |
| JP | 2008539007 A | 11/2008 |
| JP | 2009507780 A | 2/2009 |
| WO | 2006004595 A2 | 1/2006 |
| WO | 2006116252 A2 | 11/2006 |
| WO | 2007022403 A2 | 2/2007 |
| WO | 2012106735 A2 | 8/2012 |
| WO | 2013040542 A1 | 3/2013 |
| WO | 2013130655 A1 | 9/2013 |

OTHER PUBLICATIONS

International Search report in related International application No. PCT/US2012/055726, mailed Dec. 27, 2012.

International Preliminary Report on Patentability and Written Opinion in related International application No. PCT/US2012/055726, issued Mar. 18, 2014.

International Preliminary Report on Patentability and Written opinion in related International application No. PCT/US2012/031923, issued Aug. 6, 2013.

International Search report in related International application No. PCT/US2012/031923, mailed Jul. 12, 2012.

European Supplementary Search Report, EPO's Opinion and Transmitting Communication in related European patent application No. EP 12831818, Apr. 7, 2015.

International Search Report and Written Opinion in related International application No. PCT/US2014/072532, Mar. 12, 2015.

* cited by examiner

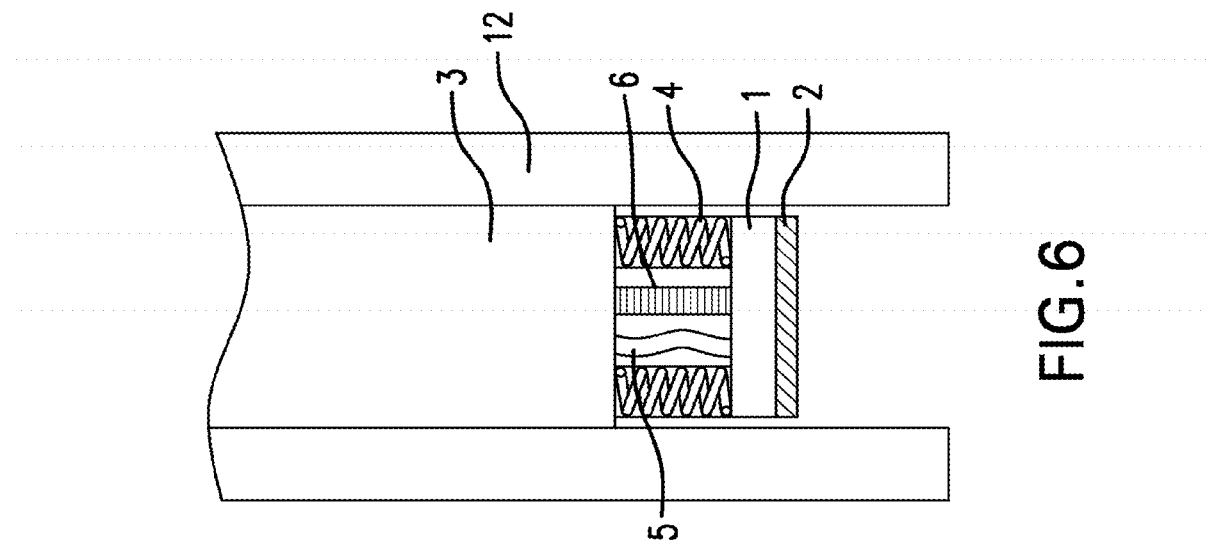
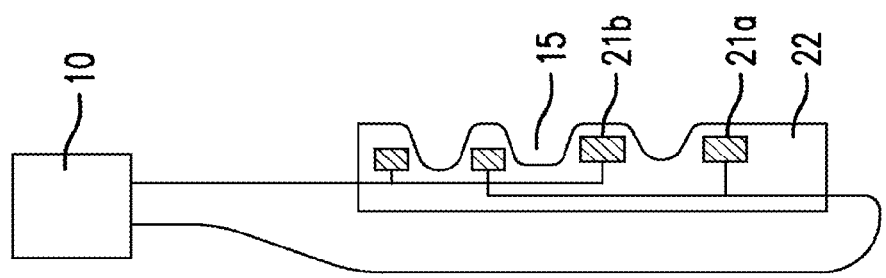

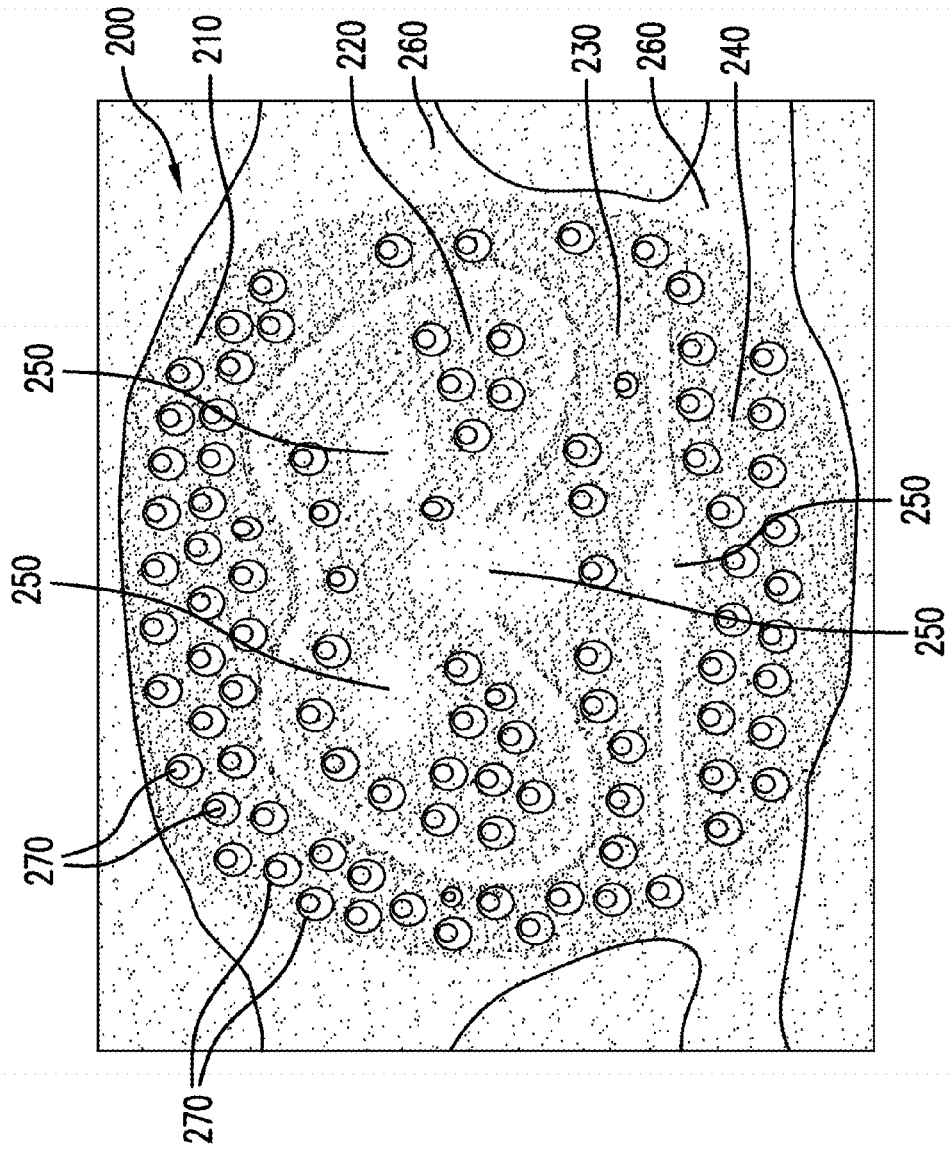

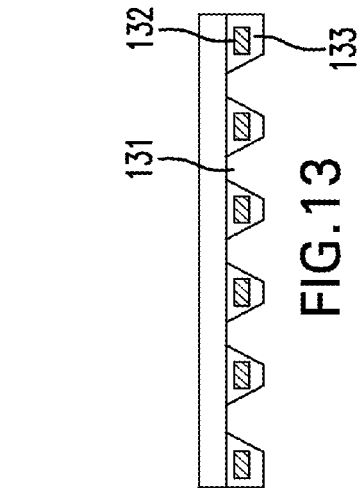
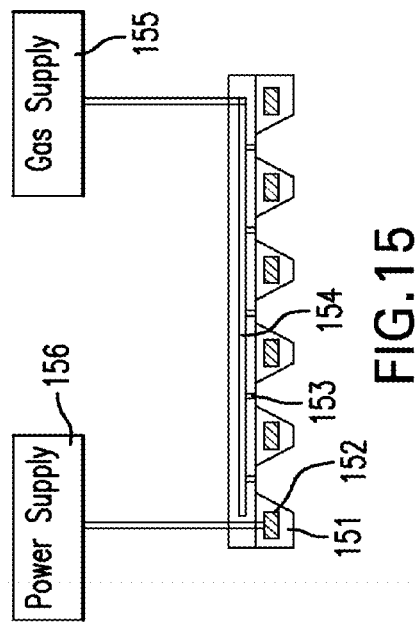
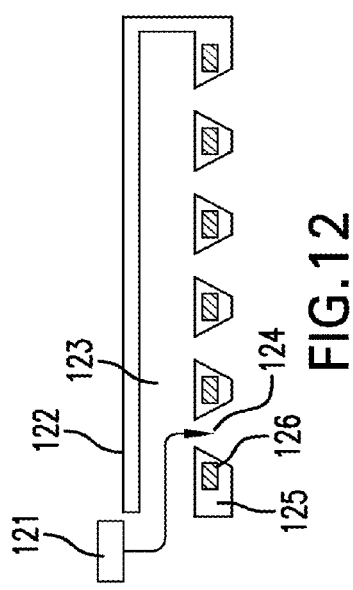
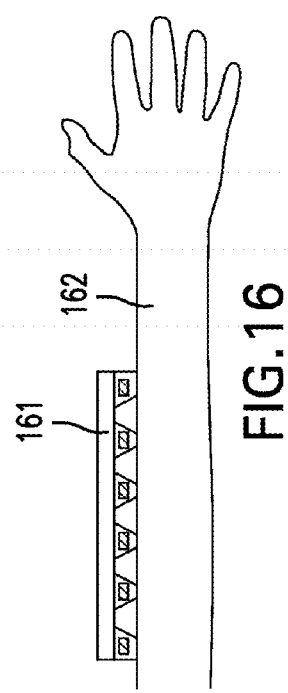

PLASMA-ASSISTED SKIN TREATMENT

CROSS-REFERENCE TO RELATED APPLICATIONS

This application is a continuation of PCT/US2012/031923 filed Apr. 2, 2012, which claims the benefit of priority of U.S. Provisional Patent Application Ser. No. 61/584,399, filed Jan. 9, 2012. The disclosure of each of the aforementioned patent applications is incorporated by reference herein in its entirety.

BACKGROUND

1. Field of the Disclosure

The present disclosure relates to methods and systems for treating skin conditions. Particularly, the present disclosure is directed to the treatment of skin conditions in a manner that is assisted and/or enhanced by use of plasma.

2. Description of Related Art

There are numerous chronic skin diseases and conditions for which there is a lack of optimal treatments. These include acne, rosacea, dermatitis, chronic wounds, actinic keratosis, basal cell carcinoma, squamous cell carcinoma, Bowen's disease, hailey-hailey disease, pemphigus, cheilitis, impetigo, cellulitis, psoriasis, and many others. There are yet additional skin conditions that are considered more "cosmetic", such as vitiligo, wrinkles (rhytids), large pores, sagging skin, lentigo (tattoos, scars, hyperpigmentation, etc.), hemangiomas, and others. Some of these conditions are caused by infectious pathogens and others are caused by problems in the immune system leading to inflammations and other symptoms. Still others are cancers or pre-cancerous lesions caused by accumulation of mutated cells. Current treatments for these indications include topical drugs, systemic drugs and electrical or laser-based heating. Each of these treatments suffers from one or more shortcomings as described below:

Topical Drugs—have some effectiveness at killing the underlying infections, but can generate pathogenic resistance, leading to decreased efficacy. Dosing cycles can also be long—they can run from 6 to 18 months in some cases—or inconvenient (multiple applications per day), which can lead to reduced patient compliance. Also, some topical drugs can cause severe skin irritation and erythema, such as imiquimod, a treatment for actinic keratosis. Yet other limitations of topical drugs and creams include the inability to inhibit recurrence of the problem.

Systemic drugs—can also be effective at killing the underlying infection, but have several potential side effects (such as liver failure) and can require relatively long dosing cycles (daily pills up to 6 months). Common examples include terbinafine and itraconazole.

Electrical or laser-based heating—various approaches have been attempted. However, most involve attempting to provide the heat required to kill the pathogen while preserving the underlying tissue. These attempts have proved difficult to implement in practice due to poor control of the heat distribution. This poor localization of the heat can lead to damage to the surrounding tissue or limited effectiveness in achieving the desired effect on the targeted tissue. The present disclosure presents improvements on the state of the art as set forth hereinbelow.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

To achieve these and other advantages and in accordance with the purpose of the disclosure, as embodied herein, the disclosure includes a variety of exemplary skin treatment methods and associated systems using plasma, preferably plasma sustained at atmospheric pressures. For example, the plasma can include a corona discharge plasma, a dielectric barrier discharge plasma, a microdischarge plasma, an inductively coupled plasma, a microwave induced plasma and/or capacitively coupled radio frequency induced plasma. In one embodiment, the plasma is generated over the surface of a treatment device, which extends toward the surface of the treated skin in some spots. In another embodiment, a high electric field is created in air that is proximal to skin and the skin serves as the second electrode. When the electric field exceeds the air/gas breakdown field, plasma will be created. The plasma can be sustained in the same way as conventional dielectric barrier discharge or pulsed corona discharge by pulsing or otherwise time varying the voltage applied to the air that is proximal to the skin.

Plasma can also be created on or proximate the surface of hair that protrudes from the skin. In this embodiment, the plasma is created in air or other gaseous media that is in contact with the desired hair surfaces. For example, a dielectric barrier discharge plasma can be created using a suspended or floating electrode whereby the hair protruding from the skin guides the plasma along its surface into the skin. Alternately, a plasma "jet" can be created, whereby the plasma is formed within an electrode system and then directed at the target skin or hair surface via pressurized gas flow or a magnetic field.

One of the problems appreciated by Applicant with maintaining a sufficiently powerful plasma discharge in close proximity to the skin is the tendency for the plasma to self-organize into multiple microdischarges and for these microdischarges to form in specific locations (such as the high spots) between the skin and the electrode. For some skin treatments, such as for treating infections or inflammations spread throughout some area of the skin, this feature is not desirable because the plasma intensity including electron concentration, radical concentration, gas temperature can be so large within the microdischarge as to cause local damage, erythema, irritation, and pain. Microdischarge damage can become particularly significant if the microdischarge is remains in the same position over the treatment area. One important aspect of the present disclosure is that it provides several ways to prevent microdischarge formation and fixation, such as:

- Using electrodes with curved surfaces that come in contact with the skin in some areas to which plasma can be guided along the electrode surface avoiding formation of microdischarges that bridge the gaps between the electrode and the skin.
- Scanning the electrode rapidly (manually or with a motor) across the skin.
- Using rapid (e.g., several or tens of nanoseconds) pulsing of the voltage waveform, such that the resulting waveform has rise and fall times durations shorter than the time required for the formation of microdischarges.
- Varying the electrode position via vibration, oscillation or other motions caused by an electrically operable vibration generation device (such as with a piezomotor or other oscillatory motor).

Using microdischarge electrodes having sub-millimeter sizes and applying them in stationary or scanning exposures.

Using the above-described techniques can facilitate the application of stronger electric fields at higher frequency, which can be expected to lead to a greater plasma intensity and shorter resulting overall treatment times, while minimizing the adverse effects associated with microdischarge formation. Use of such techniques can also increase the presence of reactive ion species ("ROS"), which Applicant believes to be beneficial.

In accordance with further aspects, the techniques disclosed herein can be used in combination with the application of particular wavelength ranges of light. In accordance with a preferred embodiment, blue light (e.g., from about 360 nm-480 nm wavelength) is also applied to tissue being treated. Thus, plasma can be applied in addition to the blue light, such that the tissue is being exposed to heat from the plasma, reactive ion species generated by the plasma, and blue light. The blue light can be generated in whole or in part by the plasma, or in combination with a second blue light source. By way of further example, most or all of the blue light can be provided from a source in addition to the plasma. Such a source of blue light can include a blue laser (e.g., GaN type), blue LED's (e.g., GaN type), mercury lamps, and the like. Blue light can be applied using a suitable dosage, such as between about 1 mJ/cm$^2$ and about 500 J/cm$^2$, between about 100 J/cm$^2$ and about 2500 J/cm$^2$, between about 150 J/cm$^2$ and about 1500 J/cm$^2$, between about 200 J/cm$^2$ and about 1000 J/cm$^2$, between about 250 J/cm$^2$ and about 1000 J/cm$^2$, between about 300 μJ/cm$^2$ and about 500 J/cm$^2$, between about 350 J/cm$^2$ and about 450 J/cm$^2$, between about 300 J/cm$^2$ and about 400 J/cm$^2$, and between about 300 J/cm$^2$ and about 350 J/cm$^2$, or any subrange in any of the aforementioned ranges of 1 mJ/cm$^2$ or multiple of 10 mJ/cm$^2$. The treatment time in which any of the aforementioned energy quantities is applied is preferably between about 0.01 seconds and about 100 seconds, between about 0.1 seconds and about 50 seconds, between about 1 second and about 25 seconds, and between about 5 seconds and about 15 seconds, or any subrange in any of the aforementioned ranges of 0.5 seconds or multiple of 0.5 seconds. Other wavelengths of light can be applied in combination with plasma to enhance the treatment effects as appropriate, such as infrared light, in any of the aforementioned combinations of energy doses and treatment times.

In accordance with further aspects, the techniques disclosed herein can be used in combination with the application of heating (via conduction, infrared light, plasma, or other electrical) or cooling. In accordance with a preferred embodiment, heating is also applied to the tissue being treated. Thus plasma can be applied in addition to the heating, such that the tissue is being exposed to heat, reactive ion species generated by the plasma, light emission from the plasma, and electric field generated within the plasma. The heat can be generated in whole or in part by the plasma or in combination with a second heating source. By way of further example, most or all of the heat can be provided from a source in addition to the plasma. Such a source of heat can included a resistive heater, convective heater (forced air), infrared LED's, heating lamps, and the like.

Additional features are disclosed herein to facilitate the safe usage of exemplary devices by untrained personnel to treat differently-shaped portions of the body. These include safety protections, control schemes, ergonomic holding structures, electrode structures, and spacing means, among other features. Estimated treatment time is preferably at least a tenth of a second and preferably no more than 1 hour, and in any desired time increment therebetween in increments of one minute or a multiple of minutes or in increments of one second or multiple seconds, as desired.

Thus, in accordance with one embodiment, a system for applying a plasma discharge is provided. The system includes an electrode adapted to be placed proximate an anatomical region of interest, a power supply in electrical communication with the electrode, the power supply being adapted and configured to apply power to the electrode to generate a plasma proximate the electrode.

In some implementations, the electrode can be flexible. The power supply can be adapted and configured to apply a pulsed voltage waveform to the electrode to generate a plasma proximate the electrode. The pulsed voltage waveform can have pulses with durations that are shorter or longer than the time required for the formation of microdischarges between the electrode and the anatomical region of interest. If desired, the electrode can be substantially inflexible. The pulse duration of the waveform can be between at least one of (i) about 0.000000010 seconds and about 0.00000010 seconds, (ii) about 0.0000000010 seconds and about 0.000000010 seconds, (iii) about 0.00000000010 seconds and about 0.0000000010 seconds, (iv) about 0.000000001 seconds and about 0.001 seconds, and (v) about 0.000001 seconds and about 0.001 seconds. The flexible electrode can include a layer of conductive material. If desired, the system can further include a flexible dielectric layer substantially surrounding the flexible electrode, the flexible dielectric layer being adapted and configured to be disposed against the anatomical region of interest. The layer of conductive material can be a continuous layer or an interrupted layer. The interrupted layer can be etched and/or a mesh, or be in a predetermined pattern. In some embodiments, at least a portion of the layer of conductive material can be transparent, and if desired, include indium tin oxide (ITO).

The dielectric layer can include a plurality of protrusions thereon for contacting the anatomical region of interest. The protrusions can have a height extending from the exterior surface between about 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, 4.5-5.0 mm, or combinations thereof. If desired, the layer of conductive material can be a conductive fluid disposed within the dielectric layer. The dielectric layer and conductive fluid can be formed into a shape matching the anatomical region of interest. The anatomical region of interest can be, for example, a face of a subject, and the dielectric layer and conductive fluid can be formed into a face mask. The electrode assembly can be configured to fit any other body part, as desired. For example, the dielectric layer and conductive fluid can be formed into a pad to be placed against the region of interest. If desired, the dielectric layer can include an adhesive layer for placement against the region of interest to hold the flexible electrode against the skin. The system can further include a removable protective layer disposed on the adhesive layer.

At least a portion of the flexible dielectric layer can be transparent to permit the plasma to be observable by a user of the system. If desired, the system can be adapted to generate a plasma over a surface of the electrode and toward the anatomical region of interest. In some embodiments, the system can further include a gas supply in operable communication with the electrode, wherein the gas supply can be adapted and configured to supply gas to the anatomical region of interest. If desired, the system can further include a fastener for holding the flexible region against the anatomical region of interest. The fastener can include at least one of (i) a hook and loop fastener, (ii) adhesive and (iii) an elastic strap, as desired.

The system can further include an exposure indicator. The exposure indicator can be adapted to indicate the amount of exposure of the anatomical region of interest to the plasma. In some embodiments, the exposure indicator can include at least one compound that reacts to the exposure from plasma. The exposure indicator can provide a visual indication of exposure to plasma. The exposure indicator can change color when exposed to plasma. The exposure indicator can include an optical sensor in operable communication with a processor adapted and configured to control the power supply. The exposure indicator can include an electrical sensor in operable communication with a processor adapted and configured to control the power supply.

In some embodiments, the system can further include a controller for controlling the power supply. The controller can be adapted and configured to receive operational data indicative of the operation of the system, to process the operational data, to determine at least one action to take in response to the processed data, and to implement the at least one action. The electrode can include a continuity sensor to determine if the electrode is in adequate physical contact with the anatomical region of interest. The continuity sensor can be adapted and configured to measure the impedance of tissue in which the sensor is in contact with. The operational data can relate to at least one of (i) a tissue impedance measurement, (ii) gas temperature, (iii) tissue temperature, (iv) light emission of the plasma, and (v) electrical current flowing into the tissue. The conditions sustaining the plasma can be modulated in response to the operational data. The conditions that are modulated can include at least one of (i) a change in the pulse shape of a waveform applied to the electrode, (ii) the frequency of the applied waveform, (iii) the voltage of the applied waveform and (iv) flowrate of a gas used to help sustain the plasma.

In further embodiments, the system can further include a ground pad for providing a ground to prevent injury to tissue in the anatomical region of interest. The ground pad can be integrated into the electrode. The ground pad can be embedded into the electrode, or can be formed about a periphery of the electrode. The ground pad can alternatively be separate from the electrode. The flexible electrode can be adapted to be applied to the anatomical region of interest without an intervening dielectric layer.

The disclosure further provides a system for applying a plasma discharge. The system includes a flexible electrode adapted to be placed proximate an anatomical region of interest, and a power supply in electrical communication with the flexible electrode, the power supply being adapted and configured to deliver power to the electrode to generate a plasma between the electrode and the anatomical region of interest. The plasma can be a corona discharge plasma, a dielectric barrier discharge plasma, a microdischarge plasma, an inductively coupled plasma, a microwave induced plasma, or a capacitively coupled radio frequency induced plasma.

In some embodiments, the flexible electrode can include a layer of conductive material. The system can further include a flexible dielectric layer substantially surrounding the flexible electrode, the dielectric layer being adapted and configured to be disposed against the anatomical region of interest. The layer of conductive material can be a continuous layer or an interrupted layer. The interrupted layer can be etched, and/or be a mesh. The layer of conductive material may be, transparent, and may include indium tin oxide (ITO), as desired.

In further aspects, the dielectric layer can include a plurality of protrusions thereon for contacting the anatomical region of interest. The flexible electrode can include a plurality of spaced conductors. The power supply can be adapted to apply power sequentially over the spaced conductors when generating the plasma to avoid microdischarges. The system can include an oscillator for generating mechanical vibration in the electrode to cause movement of the electrode when the system is operating. For example, the oscillator can include a piezomotor for inducing the mechanical vibration in the electrode. The piezomotor can have a resonance frequency between about 1.0 kHz and about 1.0 MHz. The piezomotor can have a resonance frequency between about 10 kHz and about 50 kHz. The piezomotor can have a resonance frequency between about 100 kHz and about 900 kHz. The piezomotor can have a resonance frequency between about 400 kHz and about 600 kHz.

In accordance with further aspects, the electrode can include a plurality of spaced apart conductors having a width between about 0.1 and about 2.0 mm. The conductors can be separated from each other by a distance between about 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, 4.5-5.0 mm, or combinations thereof.

The disclosure further provides a method of generating a plasma discharge. The method includes providing an electrode adapted to be placed proximate an anatomical region of interest, and applying a pulsed voltage waveform to the electrode to generate a plasma proximate the electrode, the pulsed voltage waveform having pulses with durations that are shorter than the time required for the formation of microdischarges between the electrode and the anatomical region of interest. The waveform can have a pulse duration between at least one of (i) about 0.000000010 seconds and about 0.00000010 seconds, (ii) about 0.0000000010 seconds and about 0.000000010 seconds, and (iii) about 0.00000000010 seconds and about 0.0000000010 seconds. The electrode can be flexible.

The power deposited by the plasma on the anatomical region of interest can be between about 1.0 milliwatts per square centimeter and about 10.0 watts per square centimeter. The power deposited by the plasma on the anatomical region of interest can be between about 10.0 milliwatts per square centimeter and about 1.0 watts per square centimeter. The power deposited by the plasma on the anatomical region of interest can be between about 100.0 milliwatts per square centimeter and about 0.5 watts per square centimeter. The anatomical region of interest can be exposed to the plasma for between about one tenth of a second and about one hour. The anatomical region of interest can be exposed to the plasma for between about five seconds and about fifteen minutes. The anatomical region of interest can be exposed to the plasma for between about thirty seconds and about ten minutes. The anatomical region of interest can be exposed to the plasma for between about three minutes and about seven minutes.

The disclosure provides a method of treating a disorder in a treatment area. The method includes generating a plasma proximate the treatment area, and causing reactive ion species in the plasma to interact with tissue in the treatment area including the disorder. The disorder can be on or in an animal or human. The disorder can be rhytids, wrinkles, actinic keratosis, solar letigenes, viral papillomata, scarring, seborrhoeic keratoses, sun spots, superficial skin lesions, basal cell carcinoma, squamous cell carcinoma, or melanoma, actinic keratoses, or Bowen's disease, among others. The plasma can be a corona discharge plasma, a dielectric barrier discharge plasma, a microdischarge plasma, an inductively coupled plasma, a microwave induced plasma, a plasma jet, or a capacitively coupled radio frequency induced plasma.

In further aspects, the method can further include controllably flowing a gas proximate the treatment area. The gas composition and flowrate can be selected to accomplish at least one of (i) exposing the treatment area to a desired wavelength spectrum of light, (ii) heating the treatment area, (iii) directing electrical current through the treatment area and (iv) delivering chemical species to the treatment area. Reactive oxygen chemical species are delivered to the treatment area in accordance with any embodiment herein. The wavelength spectrum and the intensity of the light can be selected to stimulate blood flow to the treatment area. At least some of the light can be in (i) the near-infrared range, (ii) the infrared range, (iii) the ultraviolet range and (iv) the visible range. At least some of the light can be in the UVA range, and the method can further include applying psoralen to the treatment area. Reactive nitrogen species can be present in the plasma. At least some of the light can be in the UVB range, and the skin disorder can be psoriasis or vitiligo. The methods can further include directing plasma along hair toward the skin in the treatment area. The methods can further include applying a sensitizing material to the treatment area prior to application of the plasma to the treatment area. Similarly, the methods can include applying a blocking material to tissue proximate the treatment area to protect the tissue from plasma.

In accordance with further aspects, the power deposited by the plasma on tissue in the treatment area including the disorder can be between about 10.0 milliwatts per square centimeter and about 1.0 watts per square centimeter. The power deposited by the plasma on the tissue in the treatment area including the disorder can be between about 100.0 milliwatts per square centimeter and about 0.5 watts per square centimeter. The tissue in the treatment area including the disorder can be exposed to the plasma for between about thirty seconds and about ten minutes in any desired time increment of one second. For example, the tissue in the treatment area including the disorder can be exposed to the plasma for between about three minutes and about seven minutes.

The disclosure further provides a method of treating an infection in a treatment area. The method includes generating a plasma proximate the treatment area, and causing reactive ion species in the plasma to interact with infected tissue in the treatment area. The infection can be on or in an animal or human. The infection can be a bacterial, fungal, viral, or parasitic infection. The plasma can be a corona discharge plasma, a dielectric barrier discharge plasma, a microdischarge plasma, an inductively coupled plasma, a microwave induced plasma, a plasma jet, or a capacitively coupled radio frequency induced plasma. The method can further include controllably flowing a gas proximate the treatment area. The gas composition and flowrate can be selected to accomplish at least one of (i) exposing the treatment area to a desired wavelength spectrum of light, (ii) heating the treatment area, (iii) directing electrical current through the treatment area, (iv) delivering chemical species to the treatment area. Reactive oxygen chemical species can be delivered to the treatment area. The wavelength spectrum and the intensity of the light can be selected to stimulate blood flow to the treatment area. At least some of the light can be in (i) the near-infrared range, (ii) the infrared range, (iii) the ultraviolet range and (iv) the visible range. The method can further include applying a sensitizing material to the treatment area prior to application of the plasma to the treatment area, and/or applying a blocking material to tissue proximate the treatment area to protect the tissue from plasma.

In some further aspects, the power deposited by the plasma on tissue in the treatment area including the disorder can be between about 10.0 milliwatts per square centimeter and about 1.0 watts per square centimeter. The power deposited by the plasma on the tissue in the treatment area including the disorder can be between about 100.0 milliwatts per square centimeter and about 0.5 watts per square centimeter. The tissue in the treatment area including the disorder can is exposed to the plasma for between about thirty seconds and about ten minutes. The tissue in the treatment area including the disorder can be exposed to the plasma for between about three minutes and about seven minutes.

The disclosure further provides a system for generating a plasma discharge. The system includes an inflatable member including at least one electrode, and a power supply in electrical communication with the flexible electrode, the power supply being adapted and configured to apply power to the electrode to cause a plasma to be generated between the electrode and an anatomical region of interest. The system can further include a dielectric layer substantially surrounding the electrode, the dielectric layer being adapted and configured to be disposed against the anatomical region of interest, wherein the plasma is generated between the dielectric layer and the anatomical region of interest. The dielectric layer can be a portion of the inflatable member, and the at least one electrode includes a conductive medium that is used to selectively inflate the inflatable member. The dielectric layer can form a plurality of protrusions on an exterior surface of the inflatable member, wherein the protrusions act to space at least a portion of the exterior surface of the inflatable member from the anatomical region of interest. The protrusions can have a height extending from the exterior surface between about 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, 4.5-5.0 mm, or combinations thereof. The protrusions can be separated by a distance between about 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, 4.5-5.0 mm, or combinations thereof. The protrusions can include at least one of bumps, ridges and undulations.

The disclosure further provides a method, including providing an inflatable member including at least one electrode, introducing the inflatable member into a region to be treated in a deflated state, inflating the inflatable member to an inflated state, disposing the electrode proximate tissue to be treated, and activating a power supply in electrical communication with the flexible electrode, the power supply being adapted and configured to apply power to the electrode to cause a plasma to be generated between the electrode and the tissue to be treated. The inflatable member can include a dielectric layer substantially surrounding the electrode, and the dielectric layer can be adapted and configured to be disposed against the tissue to be treated. The inflatable member can be inflated with a conductive medium that carries electrical current when the plasma is generated. The conductive medium can contact an electrode formed into the inflatable member to complete an electrical circuit to generate the plasma. In another implementation, the conductive medium can form the electrode.

In accordance with further aspects, the method can further include providing an exposure indicator, the exposure indicator being adapted to indicate the amount of exposure of the tissue to be treated to the plasma, and detecting the exposure of the tissue to the plasma. The exposure indicator can include at least one compound that reacts to the exposure from plasma. The exposure indicator can provide a visual indication of exposure to plasma. The method can further include applying a sensitizing material to the tissue to be treated prior to application of the plasma and/or applying a blocking material to tissue proximate the treatment area to protect the tissue proximate the treatment area from plasma.

The disclosure further provides a processor-readable computer program stored on a tangible non-transient medium for operating a plasma treatment device including a controller, a power source operably coupled and controlled by the controller, and an electrode in operable communication with the power source and controller. The program includes instructions to cause the controller to operate the power source to induce a plasma between the electrode and a treatment area, or any other method step or aspect of any system recited in this disclosure. For example, the plasma treatment device can further include a controllable gas delivery system for directing gas to the treatment area, and the computer program can further include instructions for controlling the flow of gas to the treatment area.

It is to be understood that both the foregoing general description and the following detailed description are exemplary and are intended to provide further explanation of the embodiments disclosed herein. The accompanying drawings, which are incorporated in and constitute part of this specification, are included to illustrate and provide a further understanding of the methods and systems of the disclosure. Together with the description, the drawings serve to explain the principles of the disclosed embodiments.

BRIEF DESCRIPTION OF THE DRAWINGS

FIG. 5 is a schematic showing an exemplary microdischarge array connected to a power supply and control system.

FIG. 6 is a schematic showing an exemplary electrode coupled to an electrically controllable vibration generator.

FIG. 11 is an exemplary embodiment of a flexible treatment device in accordance with the disclosure.

FIG. 12 is a cross sectional view of a flexible plasma emitter in accordance with the disclosure.

FIG. 13 is a cross sectional view of a further flexible plasma emitter in accordance with the disclosure.

FIG. 14 is a cross sectional view of an exemplary inflatable plasma emitter in accordance with the disclosure.

FIG. 15 is an exemplary system in accordance with the present disclosure.

FIG. 16 illustrates a flexible plasma emitter in accordance with the disclosure being applied to an arm of a patient.

DETAILED DESCRIPTION

Figure 1:
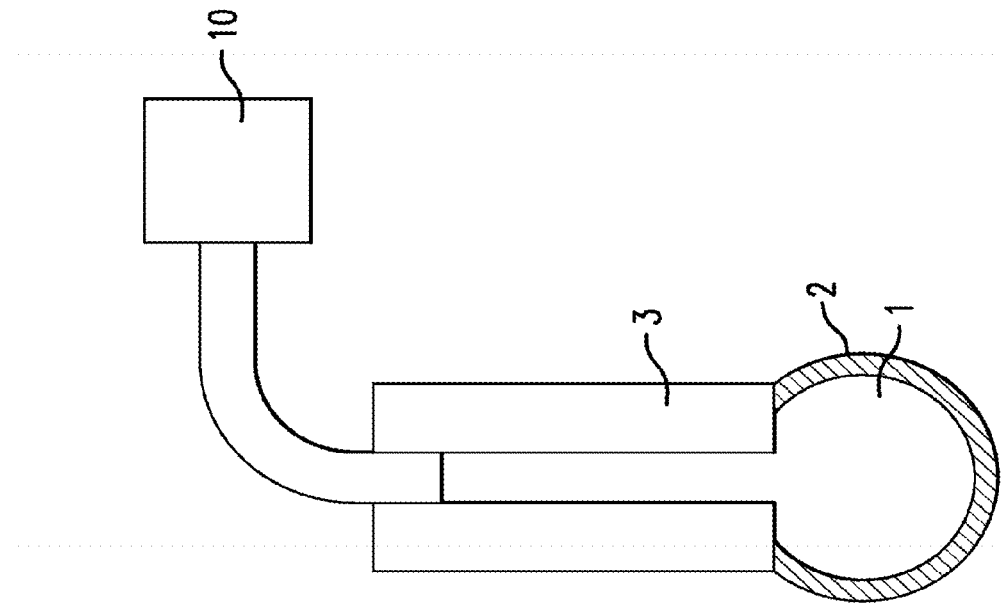
FIG. 1 is a schematic showing an exemplary electrode having a treatment end covered by a dielectric.

Reference will now be made in detail to the present preferred embodiments of the disclosure, examples of which are illustrated in the accompanying drawings. The methods and corresponding steps of the disclosed embodiments will be described in conjunction with the detailed description of the exemplary systems.

By way of introduction, plasma, sometimes referred to as the "fourth state of matter", typically includes partially and/or fully ionized gas molecules and can be produced and directed in a variety of ways and geometries. More specifically, a plasma can be thought of as a gas having molecules that can be partially or fully ionized and electrons that have kinetic energy sufficient to strip at least one electron from at least one of the gas molecules through collisions, such that the resulting plasma includes a mixture of positively charged ions in a sea of free electrons that may or may not also include neutral species mixed therewith. Plasmas can be used for a variety of purposes, including sterilization, blood coagulation, ozone generation, chemical processing, light sources, ion sources (for propulsion) and heat sources, among others. As a result of the relative simplicity of the construction of gas discharges as opposed to other emitters, such as solid state lasers, it is possible to create a variety of structures to provide a distributed energy source at an economical cost. Perhaps the best example of such arrays is the plasma television.

In accordance with the present disclosure, skin treatment methods and related systems have been developed using atmospheric pressure plasmas, that is to say, plasmas that can exist in a room environment at standard conditions or conditions that vary slightly therefrom (e.g. at standard temperature and pressure "STP"). The plasma can be a corona, dielectric barrier discharge, microdischarge; inductively coupled plasma, microwave induced plasma, or capacitively coupled radio frequency induced plasma. The plasma can also be induced as the result of a laser exposure. In one embodiment, plasma is created in proximity to the skin for a duration of at least one tenth of a second and no more than one hour, or any duration therebetween in increments of one or more minutes, one or more seconds, or one or more tenths of seconds, as desired. The plasma produces reactive chemical species such as hydroxyl radicals (OH), nitrous oxide ($NO_2$), nitric oxide (NO), ozone ($O_3$), superoxide ($O_2^-$) that kill the pathogens responsible for skin conditions such as acne. The plasma also emits light of a variety of wavelengths, generates heat, ions, and electrons. The combination of these species and energy emissions can react with or cause reactions within the skin that can affect the local cellular makeup, inflammation or other cellular processes and thereby alleviate the symptoms of such skin conditions as psoriasis, atopic dermatitis, and vitiligo. Acne, for example, has multiple causes, including comedogenesis (blockage of the sebaceous glands), excess sebum (oil) production, infection via *p. acnes*, and inflammation. In fact, the bacteria, *p. acnes*, feeds on the sebum and lives in the clogged pores. These pores typically do not consist of "living" tissue. Other embodiments are also presented.

Figure 2:
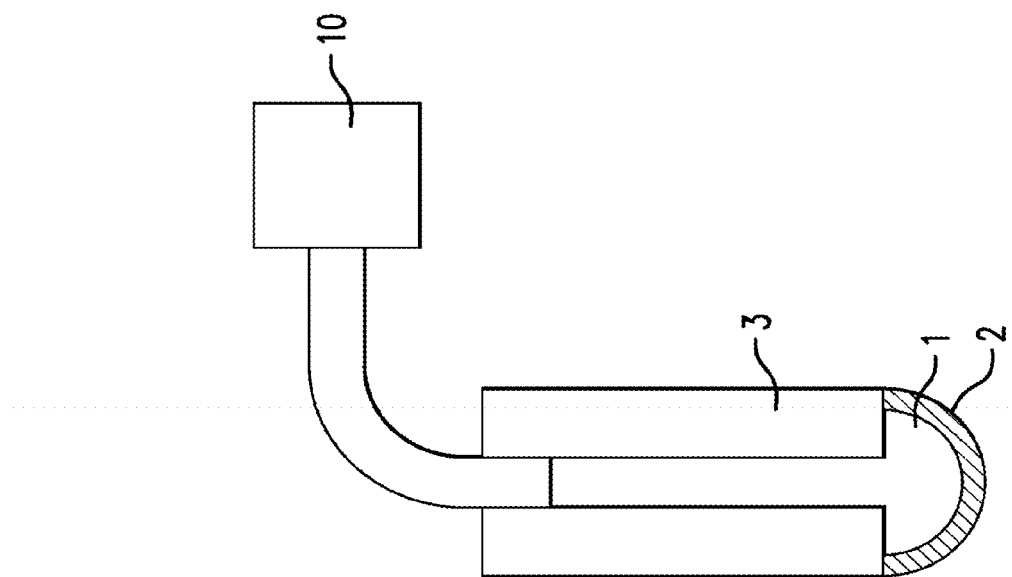
FIG. 2 is a schematic showing an exemplary electrode having a spherical treatment end.
Figure 4:
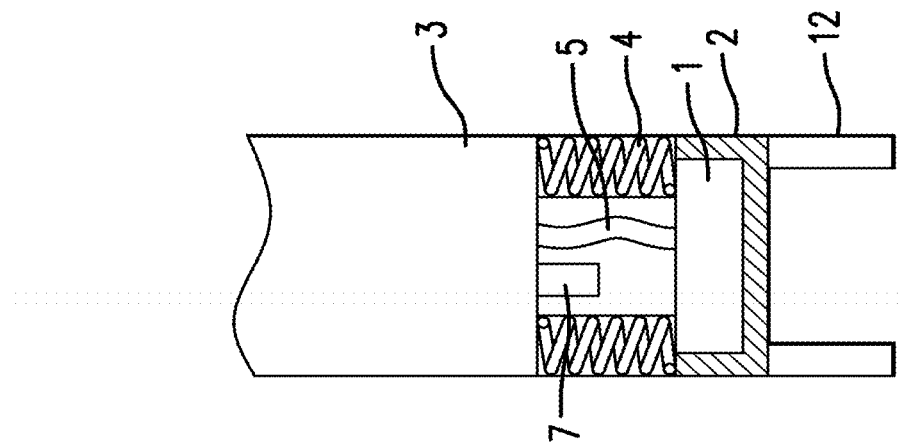
FIG. 4 is a schematic showing an exemplary electrode coupled to a spring to help minimize application force variation.
Figure 3:
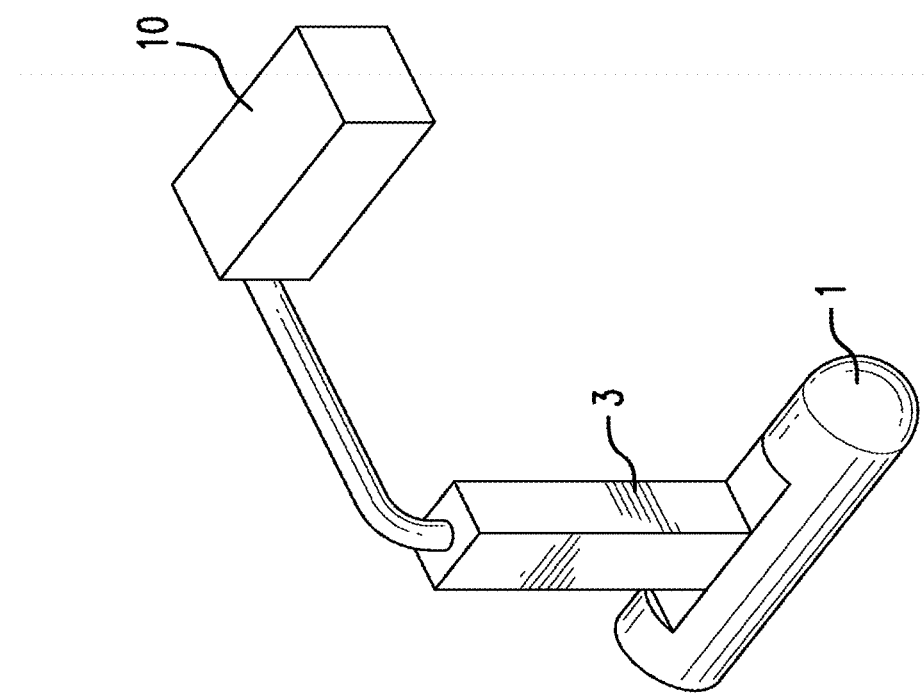
FIG. 3 is a schematic showing an exemplary electrode having a cylindrical treatment end.
Figure 9:
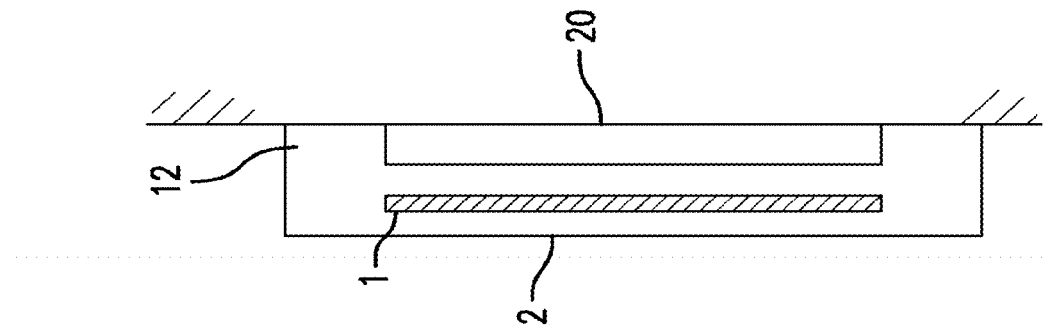
FIG. 9 is a schematic showing an exemplary flexible treatment electrode with an integrated spacer.
Figure 8:
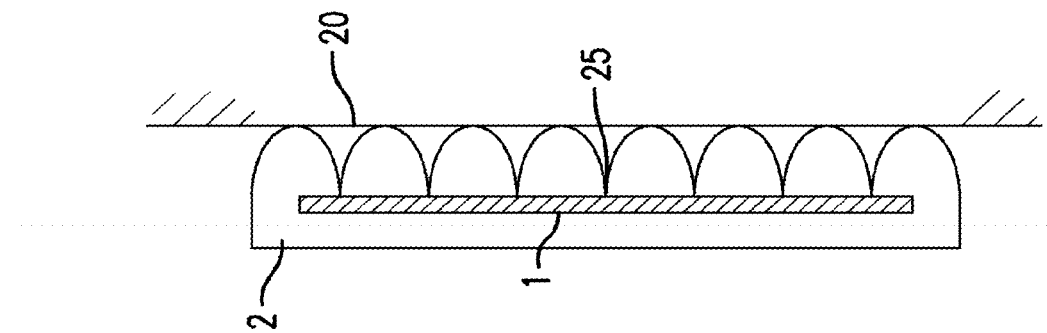
FIG. 8 is a schematic showing an exemplary treatment electrode employing small holes to help initiate the plasma formation at lower voltages and/or less complex waveforms.
Figure 7:
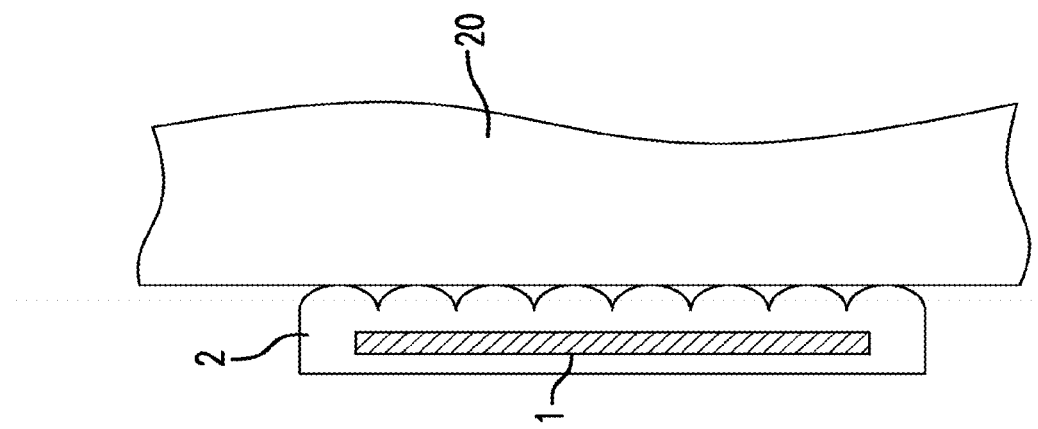
FIG. 7 is a schematic showing an exemplary treatment electrode employing a surface plasma.

For purposes of illustration only, and not limitation, FIG. 1 shows a schematic of an exemplary curved treatment electrode 1, covered by a dielectric layer 2 and electrode support 3. The electrode 1 is connected to a power supply and control system 10. FIG. 2 shows a schematic of a spherical treatment electrode 1, covered by a dielectric layer 2 and connected to a power supply and control system 10. FIG. 3 shows a cylindrical treatment electrode 1, connected to an electrode support structure 3, which is connected to a power supply and control system 10. Alternatively, the electrode support structure 3, can contain the power supply and control system 10, which enables the device to become hand held. FIG. 4 shows a detailed cross-sectional schematic of a treatment electrode 1 covered by a dielectric layer 2, joined with a mechanical spacing means/spacer 12, and connected by spring(s) 4 and an electrical cable 5 to an electrical support structure 3. The spacing means 12 optionally has a second, grounding electrode (not shown). A hard stop 7 prevents overcompression of the springs 4. FIG. 5 shows a schematic of a microdischarge electrode array having a base dielectric substrate 22, electrical cathode conductors 21a, electrical anode conductors 21b, and microcavities 15. The conductors are connected to a power supply and control system 10. FIG. 6 shows a detailed cross-sectional schematic view of a treatment electrode 1, covered by a dielectric layer 2, which is connected to an electrical support structure 3 via spring(s) 4, an electrical cable 5, and an electrically controllable vibration generator 6 (such as a piezomotor). The electrical support structure 3 has a spacer 12 mounted to it or integral to it, which optionally constrains the motion of electrode 1 and which optionally has a second, grounding electrode (not shown). FIG. 7 shows a side cross sectional schematic view of a treatment electrode 1, covered by a dielectric layer 2, which is brought in contact to an area of the body 20. The dielectric layer 2 has a varying surface profile that leads to gaps being defined between the main dielectric layer and the body 20. The treatment electrode 1 is connected to a power supply and control system (not shown). FIG. 8 shows a side cross sectional schematic view of a treatment electrode 1, covered by a dielectric layer 2, which has multiple small holes 25. The dielectric layer 2 is brought in contact to an area of the body 20. The dielectric layer may or may not have a varying surface profile that leads to gaps between the main dielectric layer and the body 20. The treatment electrode 1 is connected to a power supply and control system (not shown). FIG. 9 shows a side cross-sectional schematic of a flexible treatment electrode 1, covered by a dielectric layer 2. A spacer 12, permits the device to maintain a specific gap between the treatment electrode 1, and the body 20. The treatment electrode is connected to a power supply and control system (not shown).

In accordance with the disclosed embodiments, the treatment electrode may include multiple materials and have multiple shapes and surface finishes. Some example materials include aluminum or other conductor and alumina ($Al_2O_3$) dielectric, copper or other conductor and silicon nitride dielectric, conductor and quartz dielectric, conductor with rubber or plastic dielectrics (such as a metal conductor with silicone or epoxy with or without glass reinforcement), and conductor with a foam dielectric (such as silicone, polyurethane, or polyethylene foam). The choice of the dielectric material is based on the dielectric breakdown strength, dielectric constant, and the intended duration of usage. Some material combinations may be more suitable for long-term usage (such as copper and quartz), whereas other material combinations may be more suitable for short-term or single time usage. In the case of a foam dielectric, the pores of the foam are designed such that a microdischarge may form in each of a plurality of pores. These microdischarges are sufficiently numerous such that no individual microdischarge has sufficient energy to cause damage, pain, erythema, or irritation. The dielectric layers have a minimum thickness of about 10 microns and are attached to the conductor, for example, by molding, laminating, bonding, brazing, welding, mechanical joining. Alternatively, the dielectric layer may be applied via a coating process, such as anodizing or thermal spraying or by an oxidation process. The shape of the conductor may be flat or curved, which will affect the distribution, location and intensity of the plasma created. If the treatment electrode is smaller than the affected skin area, then the operator will have to sweep the electrode over the desired treatment area to generate the plasma where required. Alternately, the treatment electrode may have the same size or substantially the same size as the desired treatment area, in which case the operator can apply the electrode in contact with the desired treatment area and maintain its position for the duration of treatment. The connection of the treatment electrodes to the electrical support structure may be rigid or adjustable.

In order to prevent formation of powerful microdischarges that bridge the gap between the electrode surface and skin and remain in one specific location on the skin for a period longer than about 1 second, one or more of the following exemplary techniques can be used:

Electrodes having non-uniform air (gas) gap and some portions of the electrode surface extending so as to be in or near contact with skin can be used to create plasma on the electrode surface and guide this surface plasma toward the skin localizing around the point of contact or near contact between the electrode and the skin.

Scanning the electrode rapidly (manually or with a motor) across the skin so as to treat areas that may not be sufficiently exposed to the plasma when the electrode is immobile.

Use of high voltage waveforms that are similar to pulses having rise time and fall time in the range between 1 picosecond and 100 nanoseconds so as to form plasma where strong microdischarges do not have sufficient time to be created.

Varying the electrode Z-position (that is, the gap between the electrode and the skin) via vibration, oscillation or other motions (such as with a piezomotor or other oscillatory motor) such that plasma is formed between different portions of the electrode area and the skin, depending on the magnitude of the gap.

Use of microdischarge electrodes having sub-millimeter sizes and applying them in stationary or scanning exposures.

As shown in FIG. 8, small openings or holes can be defined in the dielectric layer. These holes can change the nature of the plasma discharge. The characteristic dimension of the microdischarges is on the order of 100 to 200 microns (diameter). As shown in FIG. 7, when the hole diameter is significantly smaller than the microdischarge diameter, the amount of current that can be passed through the hole to the electrode can be significantly restricted permitting generation of non-thermal plasma possibly even without AC voltage waveform typical of a dielectric barrier discharge.

In the case of pulsed operation, devices and associated methods are provided that provide pulsed voltages over time with very short duration. In accordance with one embodiment, the pulse duration can use any suitable voltage and be between about 0.010 seconds and about 0.10 seconds. In accordance with another embodiment, the pulse duration is between about 0.0010 seconds and about 0.010 seconds. In accordance with still another embodiment, the pulse duration is between about 0.00010 seconds and about 0.0010 seconds. In accordance with yet another embodiment, the pulse duration is between about 0.000010 seconds and about 0.00010 seconds. In accordance with another embodiment, the pulse duration is between about 0.0000010 seconds and about 0.000010 seconds. In accordance with still another embodiment, the pulse duration is between about 0.00000010 seconds and about 0.0000010 seconds. In accordance with a further embodiment, the pulse duration is between about 0.000000010 seconds and about 0.00000010 seconds. In accordance with still a further embodiment, the pulse duration is between about 0.0000000010 seconds and about 0.000000010 seconds. In accordance with yet a further embodiment, the pulse duration is between about 0.00000000010 seconds and about 0.0000000010 seconds. In accordance with another embodiment, a waveform is provided with a combination of pulses selected from the durations set forth above. Use of pulses of such short duration are believed to result in decreased streamer (microdischarge) formation on the basis that the pulse is too short for the plasma to organize itself in a manner in which it can form a streamer (microdischarge). It is also believed that use of such pulsing can result in a large amount of reactive ion species for treating the skin. Moreover, it is possible to not use a dielectric material between the electrode and skin when using pulses of such short duration, since the power applied to the area being treated is controlled by microprocessor; although a dielectric layer can be included for safety reasons. As such, this technique of using pulses of such short duration differs from dielectric barrier discharge plasmas, which require a dielectric layer to operate. Moreover, using such short pulses also results in a more uniform plasma.

In accordance with further aspects, the disclosure provides systems and methods for generating surface plasmas and techniques for applying surface plasmas to a patient's skin.

For purposes of illustration, and not limitation, a treatment device is provided in FIG. 7. The treatment device includes a handle (not shown) and a treatment electrode including a conductor 1 surrounded at least in part by an insulating material 2 defining an outer surface that may be placed in direct contact with a patient's skin 20. The treatment device is used in this embodiment by applying a voltage to the conductor 1 such that a surface plasma is generated along the surface of the insulating material and between the surface of the insulating material 2 and patient's skin in areas where they are not in direct physical contact, and a gap is defined between the skin and the insulating material. The behavior of surface plasma is affected by a variety of variables, including the type and overall shape of insulating material 2 used, as well as the characteristics of surface of the insulating material 2.

If desired, the insulating material can be rigid or flexible. If flexible, insulating material 2 can be, for example, a silicone compound, synthetic rubber, polyurethane, or polyethylene. These can be applied to the conductor via lamination or the conductor can be plated or otherwise sprayed onto the base insulating material. If rigid, insulating material can be a moldable material, such as PTFE, PVDF, PC, PP and the like, and can be molded such as by injection molding. As will be appreciated, the texturing of the surface will have a surface finish that can be a result of the molding process or other processing. Thus, in one embodiment, such as where insulating material is injection molded, a mold having a surface finish in accordance with SPI/SPE A1, A2, A3, B1, B2, B3, C1, C2, C3, D1, D2 or D3 can be used. Moreover, if desired, the mold can have a first, rougher, surface finish in one region, and a second, smoother surface finish in another region.

Regardless as to how it is formed, the resulting surface of material 2 facing and/or contacting the skin of the patient/user can be provided with a surface having a region with a mean surface roughness Ra between about 0.01-2000 microinches, 0.1-1000 microinches, 1-100 microinches, 5-50 microinches, 20-40 microinches, 100-200 microinches, 75-125 microinches, 1-4 microinches, 4-8 microinches, 8-12 microinches, 12-20 microinches, 20-30 microinches, 30-40 microinches, 40-50 microinches, 50-60 microinches, 70-80 microinches, 80-90 microinches, 90-100 microinches, or the like.

The surface of insulating material 2 that faces and/or contacts a user's/patient's skin can be provided with one or more bumps, ridges or undulations 78 that are distinct and on a generally larger scale than the surface finish, having an average height of about 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, or 4.5-5.0 mm, among others. Distances between adjacent bumps, ridges or undulations for the foregoing examples can be between 0.01 mm-5 mm, 0.1-0.5 mm, 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, or 4.5-5.0 mm, among others.

The material of the dielectric can also be provided with pores. These pores can serve as microcavities for a plasma microdischarge. These pores may be connected to one another or be separate and distinct. Such pores could be regular, as in a capillary array, or irregular in distribution. The shape of the pores may be spherical, cylindrical, or other. The pores have a characteristic dimension of 0.001 to 0.100 mm, 0.100 to 0.5 mm, 0.5 to 1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, or 4.5-5.0 mm, among others.

If desired, insulating material can be a semiconductor material. Concentration of charge carriers (consisting of valence and conduction electrons) in semiconductors can be modulated in a variety of ways including changes in temperature, incident light and electric field inside the material. The semiconducting material properties at different locations can also be controlled through incorporation of impurities that create either excess of conduction or excess of valence electrons. Modulating charge carrier density within the semiconducting material permits to exercise control over current being delivered into the plasma. Charge carrier density within the semiconductor may also change its electron emission capabilities and the manner in which insulating material acts as an electron emitter. Furthermore, charge carrier density within the semiconducting material may result in changes of surface breakdown enabling control over surface plasma discharge on semiconductor surface.

It will be further appreciated that insulating material 2 can have a variety of different dielectric breakdown strengths, such as rubber (450-700 V/mil), Teflon (1500 V/mil), glass (2000-3000 V/mil), alumina (300-500 V/mil), polyimide (12000-18000 V/mil), PVDF (1700 V/mil), PVC, polyurethane, UHMW polyethylene, etc. By comparison, air has a dielectric breakdown strength of approximately 20 V/mil. The choice of the dielectric thickness is determined by the magnitude of the applied voltage, the gap between the dielectric and the skin (or the profile of the dielectric, in the case of a surface discharge), and the local surface profile of the skin (which includes skin surface roughness and topographical variations due to swelling, scarring, or gross curvature of the body). In such cases, a typical thickness of approximately 0.010 to 4 mm for the dielectric layer is suitable to account for the variations in the applied voltage, electrode-skin separation, skin surface profile, etc. Generally, the smaller the gap, the smaller the dielectric thickness that is required.

The minimum gap between the dielectric and the skin can be determined according to the Paschen curve, which shows the relationship between the breakdown voltage of a gas as a function of its pressure times the characteristic distance. In some embodiments, the characteristic distance is the air gap between the dielectric and the skin. For atmospheric pressures, the Paschen curve provides that minimum voltages of approximately 400 to 6000 volts are useful to generate a breakdown for gaps of approximately 0.01 to 1 mm, respectively. In order to form a plasma over a large area as opposed to a single microdischarge, significantly higher voltages are useful for generating plasma while overcoming the variations induced by the skin surface roughness, skin impedance variations, and local topographical variation of the skin. Such voltages range, for example, from about 500 to about 1000 volts, about 1000-about 10000 volts, and about 10000-about 50000 volts.

The size of the gap between the dielectric material and the skin can also conveniently be on the same order as the height of many lesions, plaques, pustules, etc. that are typically found in skin diseases such as acne, atopic dermatitis, psoriasis, etc. In such cases, a surface discharge can be expected to form preferentially at the site of the lesion or plaque if it is in contact with the dielectric layer. If the discharge is not in contact, the gap will still be reduced and the plasma (a dielectric barrier discharge) can also be expected to form preferentially at the site of the lesion or plaque.

In further accordance with the disclosure, additional features are provided to facilitate the use of plasma treatment devices by lightly trained or untrained operators. In order to maintain the same intensity of the dose of the plasma to the skin, it is useful to apply the plasma treatment electrode in close proximity to the skin (for cases where the curved electrode is not used) in a reliable and repeatable fashion. Alternatively, a spacer made from a non-conductive material can be used to set the distance between the plasma treatment electrode and the skin, as shown in FIG. 9, for example. The spacer/spacing means can be provided around the periphery of the treatment electrode, in which case it can also surround or encapsulate the local gas. By surrounding the local gas, the structure can facilitate concentration of the heat and reactive species in the desired treatment area. Such a border can also incorporate an ozone-absorbing material, such as carbon black, to absorb the ozone that is commonly generated by the dielectric barrier discharge. In some embodiments, a line, group of lines, a polygon or polygons, a post or a plurality of posts, such as in the form of an array, or other geometries at or around the central portion of the treatment area can be included in the electrode insulating material to prevent the skin from rising up inside the region defined by the spacer, which would adversely affect the maintenance of a constant gap between the treatment electrode and the body. Alternately, the spacer itself can be mounted on a spring or other resilient member that provides a defined preload contact force between the plasma treatment electrode and the skin. When combined with an overload protection interlock (such as a contact or proximity switch or sensor) to prevent operation if the spring is fully compressed, this mechanism can be used to prevent the skin from coming too close to the plasma treatment electrode.

In another embodiment, when microdischarges are employed to generate the plasma in close proximity to the skin, the size of the microcavities is preferably small enough such that the spacing between the skin and the plasma treatment electrodes can be controlled without additional spacing means, springs, or other mechanisms, as desired.

In accordance with some embodiments, the electrical output is delivered by a power supply and affects the nature of the plasma that is emitted. Thermal and non-thermal plasmas may be used. If desired, the power supply can be connected to a control system that provides control means (e.g., a controller) that controls turning the device on an off, and may be used to control the dose (or intensity) of the plasma, which can in turn be controlled by adjusting the gas flow rate, applied voltage and hence applied current, and the like. In order to maintain user safety, a variety of controls are preferably employed. At the point of application to the skin, a temperature sensor (thermocouple or infrared sensor, for example) is employed to ensure that the gas temperature does not exceed the threshold for causing pain and erythema. Also, the electrode can contain a fuse or fast circuit breaker to ensure that the current does not increase dramatically as a result of electrode damage, which can cause significant pain to the patient. This fuse or circuit breaker can also be mounted within the power supply.

If desired, the controller can control a second set of conductors proximate the plasma emitters to provide a magnetic field proximate the plasma to help influence the direction of flow of the plasma as well as its density, particularly the density of free electrons within a given volume containing the skin to be treated. Electromagnets and/or permanent magnets can be used, for example, to apply a dipole magnetic field across the skin, thus providing magnetic field lines that are substantially oblique to the nail, thus influencing the motion of reactive species across the skin being treated.

The electrodes that are used to generate the plasma are optionally configured to deliver the electrical energy simultaneously or sequentially. In this manner, the entire plasma emitter may be excited at one time or sequentially in lines, or sub-regions may be excited sequentially. The control system further provides the means (software or hard-wired) to excite the electrodes in the desired sequence. For sequential excitation, the electrodes or sets of electrodes are individually addressable by the control system. For sequential excitation, the control system provides the means to vary the intensity and duration of the exposure to the plasma. This variation is applied spatially, allowing the user to deliver different plasma exposure doses to different regions of the target skin area.

In another embodiment, a layer containing an exposure indicator is applied to the plasma treatment electrode. By using the exposure indicator, the user will obtain direct feedback about the amount and level of exposure applied to the body. The exposure indicator can contain one or more compounds that react to the exposure from plasma such that the exposure can be detected and/or metered upon removal from the skin. The indicator may change color or otherwise provide a visual indication of exposure. This change may occur immediately or after exposure to a developer or other chemical. An example of an exposure indicator is a photosensitive material that responds to the light emitted by the plasma. Another example of an exposure indicator is a material that changes color upon exposure to different pH levels or other chemical species, such as litmus paper. A combination of different materials may be employed to indicate different exposure levels. Such materials can be provided in sheet form, and can be replaced with each subsequent use of the treatment device if the device is otherwise intended to or capable of being reusable.

In some alternative embodiments, the exposure level is monitored automatically using optical sensors, electronic sensors, or a combination thereof. The optical sensors, for example, can detect visible, ultraviolet, or infrared emissions from the plasma. The electrical sensors can detect current flow or electrical field variation and the like as generated by the plasma emission. The information from these sensors can then be delivered to the power supply and control system to enable closed loop control of the exposure dose and intensity. Such closed loop control may be desirable to account for patient-specific anatomical or disease variations that affect the plasma intensity, for example. The gas delivery from the gas supply can be controlled by a valve or set of valves. In one embodiment, the operator opens the valve to provide continuous gas flow. In an alternate embodiment, the valve or series of valves is electrically controlled via the control system.

In some embodiments, there is no gas container structure. The electrodes are then used to excite the surrounding ambient air to generate the plasma. When the emitter is applied to the skin, a spacer can be used to ensure that sufficient air is available to generate the plasma that is to be directed at the skin. The spacer can define a plurality of cavities, microcavities, microchannels, or other depressions therein defining a negative skewness or pattern. Alternatively, the spacer can have positive skewness or a positive pattern, such as by defining posts, pillars, raised lines, or other structures thereon that extend above the main surface of the device. The spacing means also provides isolation of the electrodes from the skin.

In another alternate embodiment, the power supply and control system are connected to the electrode by a high-voltage cable. This cable preferably has sufficient length to enable targeting any single portion of the body or multiple areas of the body. The electrode dimensions and weight are set so to enable comfortable hand gripping while a plastic or other insulating material shields the operator from any high-voltage exposure. Alternately, the electrode may be curved (i.e. to match or nearly match the curvature of the desired treatment area—as in knee pads, face masks, elbow pads, etc.) and/or flexible (as shown in FIG. 9). A treatment electrode can have a variety of shapes, including squares, circles, rectangles, or even face masks that enable it to conform to the desired treatment area while maintaining the desired gap or surface discharge configuration as appropriate. The shape may be standardized for all patients or custom-made based on casting, molding, optical scanning or other measurement methods to create an electrode that more precisely conforms to the anatomy of the specific patient to be treated. Alternately, the electrode, power supply and control system are integrated into a single handheld unit. This unit optionally contains batteries and/or a cable port to connect to a wall outlet.

In order to treat the desired skin area with the plasma the following exemplary method can be used:

Apply the plasma treatment electrode (having a spacer/spacing means, if the electrode is flat or no spacing means if the electrode is curved) to the target area of the skin such that the dielectric-covered conductor surface(s) are aimed towards the desired treatment area. Depending on the duration of treatment, the plasma treatment electrode(s) may be held in place via hand pressure, gravity, or a securing means, such as an adhesive, hook and loop fastener (e.g., from Velcro, Inc.), latch, springs, or elastic straps.

2. Once the plasma emitter is in place, the user activates the device using a control means/controller. Once activated, the emitter delivers plasma to the target skin area. In some cases, the electrode is of sufficient size to treat the target skin area all at one time. If the electrode is smaller than the treatment area, then the user must step-and-repeat or scan the electrode over the entire treatment area.

3. Upon completion of the treatment, the user deactivates the device using a control means/controller. The control means alternatively can provide an automatic shutoff once the desired dose has been delivered.

4. The user then removes the plasma emitter from the target treatment area.

In accordance with an alternate method to treat the target skin with plasma, sensitizing and/or blocking materials can be used to provide differential dosing for different sections of the skin. Such sensitizing materials can include water-based creams, ointments, lotions, sprays, gels, or other fluids. They can also include hydrophilic materials, such as glycerin, which can be used to attract water and water-based materials. These fluids are preferably applied topically. The blocking materials can include anhydrous (such as oil-based) creams, ointments, gels, or other fluids. They can also include hydrophobic materials which are used to repel water and water-based materials. An exemplary illustrative method can have the following steps:

1. Apply the plasma sensitizing and/or blocking materials to the desired treatment region (or protection region) of the skin. In the case of sensitizing materials, it may be helpful to wait for a certain period of time (an incubation period) for the sensitizing materials to be absorbed by the target regions of the skin.

2. Apply the plasma treatment electrode to the target area of the skin such that the emission surface is aimed towards the desired treatment area. Depending on the duration of treatment, the plasma treatment electrode may be held in place via hand pressure, gravity, or a securing means, such as an adhesive, Velcro, latches, springs, or elastic straps.

3. Once the plasma treatment electrode is in place, the user activates the device using a control means. Once activated, the emitter delivers plasma to the target skin area.

4. Upon completion of the treatment, the user deactivates the device using a control means. The control means alternatively provides an automatic shutoff once the desired dose has been delivered.

5. The user then removes the plasma treatment electrode from the target treatment area.

In still another embodiment, heat, ultraviolet light, visible light, and/or infrared radiation can be applied in concert with or in alternating fashion with the plasma in order to further accelerate the killing of pathogens, alleviation of inflammation, and/or activation of other cellular processes and chemistry. In another embodiment, topical and/or systemic drugs can be used in synergistic combination with the plasma treatment in order to further increase the effectiveness and speed of killing and/or other reactions. In another embodiment, the electrode itself is heated and thereby provide conductive heating of the skin, which can combine with the non-thermal plasma to enhance the effectiveness and speed of killing and/or other reactions.

If thermal plasma or heat enhancements such as infrared radiation are employed, it may be desirable to cool the skin surrounding the skin for greater patient comfort. The skin may be cooled by flowing or spraying water or cryogen at it. Alternatively, when the electrode is in contact with the skin, it can be cooled and thereby provide conductive cooling to the local skin region. In another embodiment, after-care creams, gels, or other materials may be applied to the treated skin to help alleviate or repair pain, irritation, erythema, or other unwanted effects, such as cellular or DNA damage. For example, anti-oxidants may be used to help reduce post-treatment levels of reactive oxygen species and promote DNA repair.

In accordance with a further aspect, a plasma sensitizer can also be used. In one aspect, the sensitizer can act as a conductive fluid to direct the plasma in a desired direction, such as toward the skin. In another aspect, the sensitizer can additionally or alternatively provide chemicals that react with the plasma, thereby enabling other reactions with the skin to occur. This can result in faster reactions at the skin. Suitable materials to be used as sensitizers can include, for example, water, saline, deionized water, or any fluid containing organic compounds, as well as materials including antioxidants. The plasma sensitizing fluid can also be delivered to the skin as part of the device construction. The device can contain a spray, sponge or vapor (aerosolized fluid) jet that has the sensitizing fluid and controllably releases said fluid as desired by the user or automatically upon contact by the electrode to the skin. Finally, a moistened fabric may be placed between the electrode and the skin. In this case, the discharge will occur within the cloth and excessive streamer formation will also be avoided.

Figure 10:
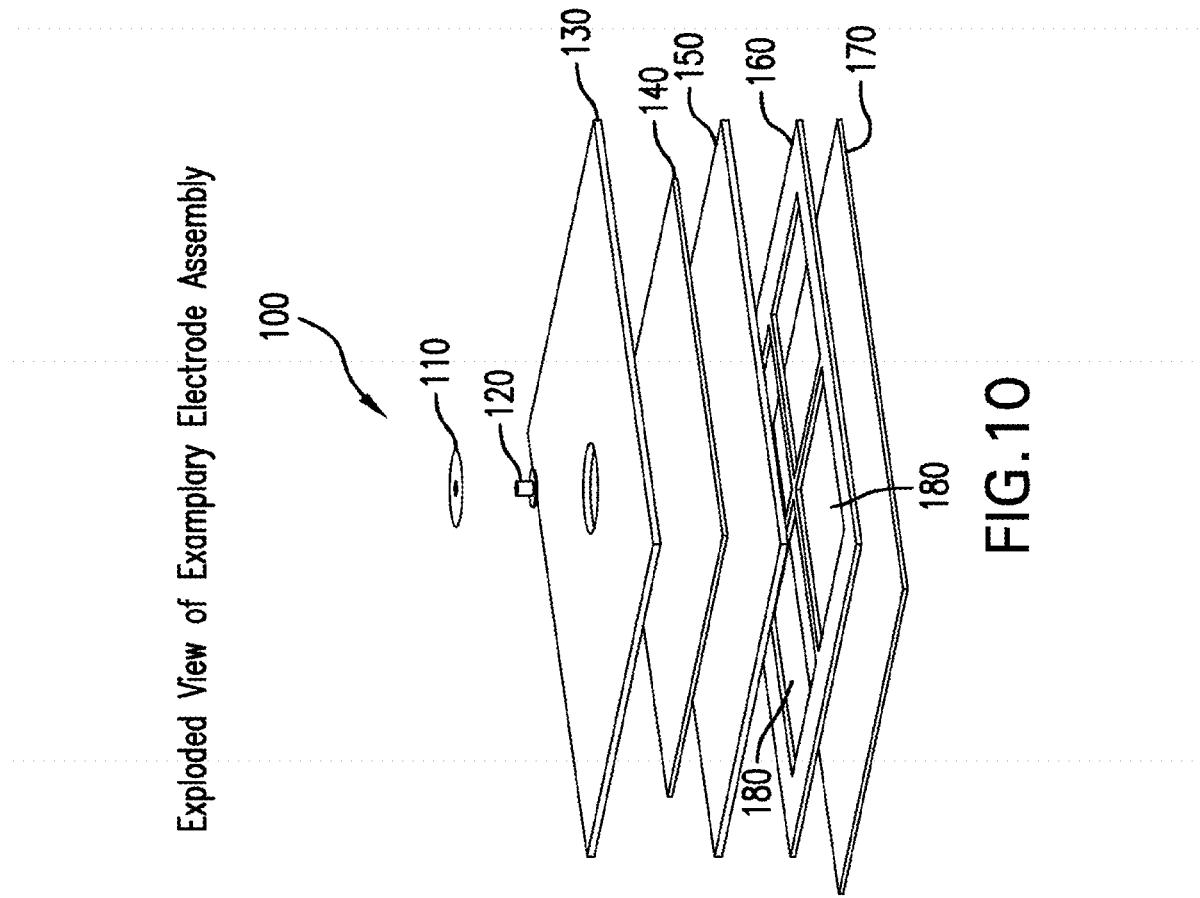
FIG. 10 is an exploded view of an exemplary electrode in accordance with the disclosure.

An exploded view of an exemplary embodiment of a flexible plasma emitter in accordance with the disclosure is presented in FIG. 10 and represented by reference numeral 100. The central conductor 140 of the flexible plasma emitter 100, depicted as a sheet in FIG. 10, can be made from a variety of solid sheet materials, including copper, aluminum, tin, silver, steel, among others. The plasma emitter 100 also includes a sensor stud 120, which may be made from a non-conductive material, and can include a conductive coating and a conductive adhesive for attachment to the central conductor 140. The central conductor is attached on either side to layers of dielectric material 120, 150 as described herein (e.g., polysiloxane having a shore A hardness of about 30-90) or other material. The attachment between components 130, 140, 150 may be by way of adhesive, or the like. A further layer of dielectric material 160 is also provided having one or more cut-outs 180. Layer 160 is attached to layer 150 by any desired means, or may be integral with layer 150, as desired. The cut-outs cooperate with layer 150 to form recesses or chambers in which plasma can form when placed against a patient's skin. If desired, the side of layer 160 not in contact with layer 150 that is skin-facing during use may be provided with a layer of skin-friendly adhesive and a removable backing layer 170 (e.g., of PET, paper or other material) to provide adhesion to a patient's skin. If desired, layer 150 can be provided with one or more protrusions (not shown) in order to help ensure spacing between the patient's skin and the remainder of layer 150.

While depicted as a sheet, the central conductor 140 could similarly be supplied as a mesh or other interrupted surface to help control or otherwise modify the electrical field over the device while in use. As such, the central conductor 140 may also have one or more holes, slots, etchings, openings, or pores in it. When combined with the use, for example, of transparent dielectric materials, such openings can also serve as an indicator that the plasma has been generated within the cavity of the patch because light generated by the plasma will be transmitted through the opening. Such an indicator may also be configured to provide other information, such as product branding or other messages. Alternatively, a transparent conductor, such as indium tin oxide (ITO) or conductive mesh may be employed for indication of plasma emission by transmission of light.

Alternately, the central conductor may be made from a conductive ink or powder, which may be printed, fused, or otherwise deposited onto one of the dielectric layers. The use of conductive inks may provide advantages in manufacturing through ease of automation, alignment, cost reduction, etc.

By way of further example, instead of a solid central conductor, a specific shape or array of shapes may be provided within the flexible plasma emitter. Such shape(s) can thus also define the spatial location of the plasma treatment to the body once applied. Such shapes may be standardized or custom-defined via die-cutting, laser cutting, deposition, etching, and the like. For example, it may be desirable to provide directed treatment to psoriasis plaques or other skin lesions while avoiding treatment of the surrounding, healthy skin.

In some embodiments, it is desirable to provide a treatment patch that is flexible enough to conform to the complex curvatures of the body, such as the face, while preventing exposure to non-targeted regions (such as the eyes or mouth). Normally, when a patch is made flat, it will be difficult to enable it to bend in 2 directions simultaneously without buckling. Furthermore, the thicker the patch, the more that such bending becomes difficult. To meet these needs and to overcome the problem of buckling, a patch can have simple cut-outs in the desired locations, such as the eyes and mouth, as well as slits in order to allow a nominally flat patch to flex in 2 directions simultaneously. As a further enhancement, the dielectric layers of the patch can be sandwiched together through lamination around the edges. This laminated bag structure is then filled with a viscous liquid conductive gel. By flowing around the different regions of the patch, they help the patch maintain contact with the skin over the entire area without buckling. The movement of the gel to different regions of the patch produces variations in the local stiffness of the patch, which enables variable local deformations. These variable local deformations result in the patch having more consistent contact with the body over the entire area. If desired, one or more protrusions can be provided on the mask in order to help facilitate establishment of plasmas in preselected areas.

For purposes of illustration, and not limitation, as embodied herein and as depicted in FIG. 11, an exemplary face mask 200 containing conductive fluid within a reservoir is provided. As illustrated, face mask 200 includes a peripheral portion 210 that encompasses the forehead and surrounds an inner region 220 that rests around openings 250 defined for a patient's eyes. The mask 200 includes a further medial lateral portion 230 that extends from one side of the mask 200 across to the other side of the mask 200, and generally coincides with the region of the face between a patient's upper lip and nose. The mask further includes a lower peripheral edge parallel to and partially spaced from the medial lateral portion by an opening 250 for a patient's mouth. A further opening 250 for a patient's nose can also be provided between the middle lower portion of the inner region and the middle upper portion of the medial lateral portion 230 of the mask 200. If desired, one or more protrusions or standoffs 270 can be provided on the mask to rest against the patient's skin. The protrusions can be formed by dimpling the sheet of the mask that faces the patient's skin, creating wells on the inside surface of the mask for receiving conductive fluid, thereby providing a plurality of electrodes extending from a reservoir of conductive fluid defined by two sandwiched sheets of material, such as plastic material. One sheet of the plastic material can form the outer surface of the mask and reservoir, while the inner surface that may be dimpled can form the inner surface of the mask and reservoir.

It can be desirable in some instances to provide a custom treatment patch or mask that is designed to work for a specific body part of a specific patient. Such a patch or mask may have a specific topography to enable better conformance to the patient's body. In addition or alternatively, the patch or mask may have pre-defined treatment areas within it to provide directed treatment to diseased skin while preserving healthy skin. One embodiment of making a suitable treatment patch can include the following steps:

1. Creating a mold of the treatment area of the patient using liquid silicone or other body molding compound by covering the patient's skin or a layer of material (e.g., sheet material and/or release agent) in contact with the patient's skin with the silicone material or molding compound.

2. Forming a first layer of dielectric material from the silicone material or molding compound or by making a mold from a cast of the treatment area.

3. Adding a conductive layer to the first layer in manners as described herein (e.g., by applying conductive ink, or a foil metal layer, conductive gel layer, etc.) and adding a further dielectric layer to the conductive layer to form a sandwich of the dielectric layers and conductive layer.

4. Attach, emboss or remove material from the sandwich to define a gap between the flexible plasma emitter and the patient's treatment area. Such a gap can range, for example, from 0.2 to 4 millimeters. This can be done by adding standoffs to the underside of the first layer that is to contact the treatment area, or by excavating or etching pores or other openings into the underside of the first dielectric layer.

5. Attaching a cable connector and fastener, if desired, to the custom flexible plasma emitter to attach it to the treatment area.

Another exemplary method of generating a custom treatment patch can include:

1. Image and digitize the topography of the treatment area of the patient and/or the targeted skin for treatment (e.g., diseased vs. healthy).

2. Generate a mold for the flexible plasma emitter using the digital scan of the patient treatment area.

3. Using the mold, generate the base dielectric-conductor-dielectric sandwich that comprises the flexible plasma emitter. This can include deposition of raw materials, curing, stretching, and/or sealing, etc. In this embodiment, the conductor shape can be defined digitally and applied to one of the dielectric layers (through deposition of conductive ink, for example).

4. Attach, emboss or remove material from the sandwich to define a gap between the flexible plasma emitter and the patient's treatment area. Such a gap can range, for example, from about 0.2 to 4 millimeters.

5. Attach cable connector and body fastener, if desired, to the custom flexible plasma emitter.

In order to deliver higher power levels to the body, it is desirable to provide a grounding (dispersive) pad proximately located to the flexible plasma emitter. Such pads are commonly used in conjunction with electrosurgical devices. As the current transmission increases, there is a higher risk of burning the skin. The risk of creating skin burns depends on the amount of current divided by the area over which it is distributed, which is also known as the current density. Nominally, the current density at the ground pad is defined by the area of the pad. However, there are some additional considerations:

1. The entire ground pad is preferably securely attached to the body of the patient. A partial attachment or removal of the ground pad can cause the current density to increase.

2. The ground pad preferably has sufficiently low resistance to avoid generation of heat within the pad. Such a resistance can range, for example, from about 0.1 to about 5000 ohms.

3. The ground pad preferably radiates any heat generated within the pad and/or can provide active cooling to minimize the risk of burning.

In order to ensure that the ground pad is attached securely to the patient, prior to treatment, remote monitoring of the pad attachment can be employed as follows. First, two or more pads or pad sections can be attached to the body in close proximity to one another. These pads can have matching connectors and a cable or cables that run back to the power supply and control system. Prior to and during treatment, the power supply and control system can send a small amount of current via one of the conductive pathways to one of the ground pads. It then measures the return current that is conducted by the second ground pad to determine the overall impedance of the system. If the measured impedance deviates from the nominal value, then the power supply and control system prevents the treatment from starting and/or interrupts the treatment. An indicator means (visual, audible, etc.) is provided on the power supply and control system to inform the operator that the grounding pad(s) are not fully attached to the body.

Optionally, the grounding pad(s) may be integrated with the plasma emitter. Such a construction may provide advantages in ease of application to the body, convenience, and/or lower cost. The grounding pad can be provided within the plasma emitter, for example, by providing a grounding conductor that is mounted around the periphery or other non-treatment areas of the plasma emitter. This grounding conductor is optionally mounted to the skin via a conductive skin adhesive or gel, which can also help provide the required spacing means for the plasma emitter. This conductor can be connected to the power supply through a separate connector. As in the previous discussion, it is possible to monitor the connection (and thereby the overall current density) of the patch by sending a small current to the grounding pad(s) and measuring the return current to determine the overall impedance.

The flexible plasma emitter can be connected to the power supply by a variety of techniques. For example, short wires having an external connector may be laminated, glued, soldered, or crimped onto the conductive layer of the flexible plasma emitter. Alternatively, a variety of connectors may be mounted (via soldering, lamination, or gluing) on the conductor of the flexible plasma emitter. These can include, for example, snap connectors, surface mount connectors, pin holes, crimp or clamps connectors, among others. Finally, the conductor of the flexible plasma emitter can be formed into one half of a connector, such as a conductive tab or pin. The flexible plasma emitter can be attached to the treatment area through a variety of fasteners/attachment techniques, including hook and loop fastener, straps, and skin adhesives. The skin adhesives may be single-use or multi-use, such as in the case of hydrogels.

In further accordance with the disclosure. FIG. 12 shows a cross-sectional view of a further exemplary flexible plasma emitter. An external gas supply 121 provides gas to a container 122 that has a plenum 123 to provide gas to each of the plasma emission locations, such as in 124. The emission locations can defined by a spacer, 125, which can encapsulate the electrodes 126, that are used to excite the gas to generate the plasma.

FIG. 13 shows a cross-sectional view of an exemplary flexible plasma emitter in accordance with the disclosure that uses ambient air, as in the embodiment of FIG. 12, to provide the gas for the plasma. As with the embodiment of FIG. 12, the electrodes 132 are encapsulated in an insulating layer 133 to provide a gap 131 within which a treatment plasma can be generated.

FIG. 14 shows a cross-sectional view of an exemplary flexible plasma emitter that can be inflated with a fluid (e.g. for use inside a body cavity). The emitter can include electrodes 141 encapsulated in an insulation layer 142 that also constitutes a plurality of spacers defining gaps therebetween for the formation of plasma on the surface of the inflatable device, and an interior reservoir or inflation area 143, which is connected to a conduit or tube 144. As illustrated, the tube extends outside of the treatment area (outside the body) to an external gas or liquid supply (not shown). Plasma can be generated on the outer surface of the device in voids created between the spacers. Alternatively, openings can be provided in the reservoir, and a working gas (e.g., carbon dioxide or other suitable gas) can be directed through the openings to the outer surface of the device to facilitate plasma generation.

FIG. 15 is a schematic view of the overall system of an exemplary flexible plasma emitter, including the emitter, which has a spacer 151, a series or plurality of electrodes 152, an optional gas port 153 and gas plenum 154. The gas plenum is connected to a gas supply 155. The electrodes are illustrated as being connected to a power supply and control system 156.

FIG. 16 illustrates a further exemplary method of treatment in which the flexible plasma emitter 161 is applied topically to a region of the body 162.

In the aforementioned embodiments, the flexible plasma treatment device can include a gas container configured into a flexible, plasma emitter that is applied to the body. The plasma can be a corona, dielectric barrier discharge, inductively coupled plasma, microwave induced plasma, or capacitively coupled radio frequency induced plasma. Electrodes can be placed near the gas container in order to generate the plasma. These electrodes can be connected to a power supply having the necessary electrical output characteristics to generate the desired plasma. The plasma can then be emitted via an array of holes in the container. These holes can be configured to direct plasma toward the body to provide tissue treatment. If desired, a new supply of gas can be provided by a conduit that connects the gas container to an external gas supply. This gas supply can also be used to assist the delivery of the plasma to the desired area of the body.

The electrical output delivered by the power supply can affects the nature of the plasma that is emitted. Thermal and non-thermal plasmas can both be used. Further, the power supply can be connected to a control system that provides a controller, including activation, dose (or intensity), time of exposure, and de-activation as discussed elsewhere herein. The electrodes that are used to generate the plasma can be configured to deliver the electrical energy simultaneously or sequentially. In this manner, the entire flexible emitter may be excited at one time or sequential lines, or sub-regions may be excited sequentially. The control system can provide the requisite signals (via software or hard-wired) to excite the electrodes in the desired sequence. For sequential excitation, the electrodes or sets of electrodes can be individually addressable by the control system. For sequential excitation, the control system provides the means to vary the intensity and duration of the exposure to the plasma. This variation can be applied spatially, allowing the user to deliver different plasma exposure doses to different regions of the target tissue. This feature is desirable for the preservation of healthy cells that may be adjacent to targeted cells, such as tumors or pathogens.

The gas delivery from the gas supply can be controlled by a valve or set of valves. In one embodiment, the operator can open a valve to provide continuous gas flow. In an alternate embodiment, the valve or series of valves can be electrically controlled via the control system.

In an alternate embodiment of the invention, there is no gas container structure. The electrodes can thus be used to excite the surrounding ambient air to generate the plasma, similar to other embodiments discussed herein. When the flexible emitter is applied to the body, a spacer can be used to ensure that sufficient air is available to generate the plasma that is to be directed at the body. The spacer can be a number of microcavities, microchannels, or other depressions having negative skewness as discussed elsewhere herein. Alternatively, the spacing or standoff means can have positive skewness, such as posts, pillars, raised lines, or other structures that extend above the main surface of the device as discussed elsewhere herein. The spacers can also provide isolation of the electrodes from the body. Finally, the top or back of the device (the side that does not contact the body) can have an insulating/isolating layer that encapsulates the electrodes. That is, the electrodes are preferably embedded within dielectric or insulating material.

In a further embodiment of the disclosure, the tissue treatment apparatus can be thin such that it can be inflated into a cylindrical, spherical or other round shape (e.g., FIG. 14). This shape can be placed inside a body cavity such as the brain, bladder, esophagus, lung, gut or other location in order to deliver the plasma treatment to the interior of the body cavity. An advantage of this structure is that the plasma may be delivered rapidly to the entire cavity while maintaining a uniform or controlled dose. Another advantage of this structure is that it may be used to provide mechanical support to the surrounding tissue to prevent collapse during treatment.

In order to treat the desired tissue with the plasma the following method can be used in some implementations:

1. The flexible plasma emitter can be applied to the target area of the body such that the emission surface is aimed towards the desired treatment area. Depending on the duration of treatment, the flexible plasma emitter may be held in place via hand pressure, gravity, or a securing means, such as an adhesive, hook and loop fasteners, or elastic straps. If the flexible emitter is placed inside the body, the flexible structure can be inflated into a balloon shape. This balloon shape can conform to the target body cavity. The device can be inflated by gas or liquid conductor (e.g., conducting gel), as desired. For example, a conducting gel can be used to inflate a dielectric sheath having a plurality of protrusions formed into its exterior. The protrusions can be solid, and/or can form pockets on the inside of the inflatable portion so as to accommodate conductive fluid.

2. Once the flexible plasma emitter is in place, the user can activate the device using an actuator connected to a controller. Once activated, the emitter can deliver plasma to the target tissue/treatment area.

3. Upon completion of the treatment, the user can deactivates the device using the actuator/controller. The controller can alternatively provide an automatic shutoff once the desired dose has been delivered.

4. The user can then remove the flexible plasma emitter from the target treatment area. If necessary or desired, the user can first deflate the flexible plasma emitter prior to removal from the body.

In alternative method to treat the target tissue with plasma, sensitizing and/or blocking materials can be used to provide differential dosing between healthy cells and target cells or pathogens. Such sensitizing materials can include, for example, water-based creams, ointments, lotions, sprays, gels, or other fluids. They can also include hydrophilic materials, such as glycerin, which can be used to attract water and water-based materials. These fluids can be applied topically or injected locally. The blocking materials can include, for example, anhydrous (such as oil-based) creams, ointments, gels, or other fluids. They can also include hydrophobic materials which are used to repel water and water-based materials. Such implementations can include the following steps:

1. Apply the plasma sensitizing and/or blocking materials to the desired treatment region (or protection region) of the body. In the case of sensitizing materials, it may be advantageous to wait for a certain period of time (an incubation period) for the sensitizing materials to be absorbed by the target regions of the body.

2. Apply the flexible plasma emitter to the target area of the body such that the emission surface is aimed towards the desired treatment area. Depending on the duration of treatment, the flexible plasma emitter may be held in place via hand pressure, gravity, or a fastener, such as an adhesive, hook and loop fasteners, or elastic straps. If the flexible emitter is placed inside the body, it may be advantageous or necessary to inflate the flexible structure into a balloon shape. This balloon shape can conform to the target body cavity.

3. Once the flexible plasma emitter is in place, the user or other operator can activate the device using an actuator/controller. Once activated, the emitter can deliver plasma to the target tissue.

4. Upon completion of the treatment, the user can deactivate the device using the actuator/controller. The controller alternatively can provide an automatic shutoff once the desired dose has been delivered.

5. The user can then remove the flexible plasma emitter from the target treatment area. If necessary or desired, the user can first deflate the flexible plasma emitter prior to removal from the body.

Thus, it will be appreciated that, in some implementations, a tissue treatment apparatus is provided that includes a gas container having gas exit holes, electrodes in proximity to the gas container, and a power supply connected to said electrodes and providing electrical output characteristics to generate a plasma within the gas container and/or in close proximity to the container. The gas container can be connected to an external gas supply. The plasma can be a corona, dielectric barrier discharge, inductively coupled plasma, microwave induced plasma, or capacitively coupled radio frequency induced plasma, as desired. The power supply can deliver pulses of current having a voltage of 10 volts to 60 kV where each pulse has a duration ranging from 1 nanosecond to 100 milliseconds. The gas container can be a flexible polymer or a flexible metallic film having one or more layers, as desired. If desired, the gas container and the entire apparatus can be inflatable. The electrodes can be a set of pairs that have been placed on opposite sides of each gas exit hole. The gas supply can be, for example, nitrogen, helium, oxygen, air, xenon, neon, krypton, or a combination thereof. In further implementations, a tissue treatment apparatus is provided that includes a set of electrodes, an isolation layer that encapsulates the electrodes and a spacer that provides physical separation between the isolation layer and a treatment region of the body. The entire apparatus can be inflatable. The spacing means can be one or more microcavities, microchannels, depressions, posts, pillars, raised structures, or other surface variation.

In further implementations, a tissue treatment method is provided that can include applying a flexible plasma emitter to the desired treatment region of the body such that the emission is aimed towards the desired treatment region, delivering at least one pulse of electrical energy to generate a plasma, and flowing the plasma towards the desired region of the body. A tissue treatment method is similarly provided that includes inserting a flexible plasma emitter into a desired treatment region of the interior of the body, inflating the flexible plasma emitter such that its exterior at least partially conforms to the desired shape inside the body, delivering at least one pulse of electrical energy to generate a plasma, flowing the plasma towards the desired treatment region of the body, and de-activating the plasma/plasma excitation means.

In some implementations of the methods, a sensitizing material can be applied to the desired treatment area of the body prior to application of the flexible plasma emitter. A blocking material can be applied to the desired area of the body to be protected prior to the application of the flexible plasma emitter. A method of treating an infection in a subject using the aforementioned methods is also provided. The infection can be a bacterial, fungal, viral, or parasitic infection. A method of treating a skin disorder in a subject is also provided by administering one or more of the tissue treatment regimens described herein to the subject. The skin disorder can be rhytids, wrinkles, actinic keratosis, solar letigenes, viral papillomata, scarring, seborrhoeic keratoses, sun spots, superficial skin lesions, basal cell carcinoma, squamous cell carcinoma, or melanoma, among others. Similarly, a method of treating a tumor in a subject is provided including administering the tissue treatment to the subject according to any of the aforementioned methods.

In order to address various issues and advance the art, the entirety of this application (including the Cover Page, Title, Headings, Field, Background, Summary, Brief Description of the Drawings, Detailed Description, Claims, Abstract, Figures, Appendices and/or otherwise) shows by way of illustration various embodiments in which the claimed inventions may be practiced. The advantages and features of the application are of a representative sample of embodiments only, and are not exhaustive and/or exclusive. They are presented only to assist in understanding and teach the claimed principles. It should be understood that they are not representative of all disclosed embodiments. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and functional, logical, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the invention, and inapplicable to others. In addition, the disclosure includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, functional, features, logical, organizational, structural, topological, and/or other aspects of the disclosure are not to be considered limitations on the disclosure as defined by the claims or limitations on equivalents to the claims. It is to be understood that, depending on the particular needs and/or characteristics of a MOE™ individual and/or enterprise user, database configuration and/or relational model, data type, data transmission and/or network framework, syntax structure, and/or the like, various embodiments of the MOE™ may be implemented that enable a great deal of flexibility and customization.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Descriptions herein of circuitry and method steps and computer programs represent conceptual embodiments of illustrative circuitry and software embodying the principles of the disclosed embodiments. Thus the functions of the various elements shown and described herein may be provided through the use of dedicated hardware as well as hardware capable of executing software in association with appropriate software as set forth herein.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicants thus regard any means which can provide those functionalities as equivalent to those shown herein.

Similarly, it will be appreciated that the system and process flows described herein represent various processes which may be substantially represented in computer-readable media and so executed by a computer or processor, whether or not such computer or processor is explicitly shown. Moreover, the various processes can be understood as representing not only processing and/or other functions but, alternatively, as blocks of program code that carry out such processing or functions.

The methods, systems, computer programs and mobile devices of the present disclosure, as described above and shown in the drawings, among other things, provide for improved methods, systems and machine readable programs for carrying out the same. It will be apparent to those skilled in the art that various modifications and variations can be made in the devices, methods, software programs and mobile devices of the present disclosure without departing from the spirit or scope of the disclosure. Thus, it is intended that the present disclosure include modifications and variations that are within the scope of the subject disclosure and equivalents.

What is claimed is:

1. A system for applying a plasma discharge, comprising:
a) an electrode adapted to be placed proximate an anatomical region of interest, the electrode being defined at least in part by a flexible electrode surface that is configured to conform to the curvature of the anatomical region to be treated with a plasma to create a substantially uniform gap between the flexible electrode surface and the anatomical region of interest to be treated to facilitate formation of a substantially uniform plasma across the anatomical region to be treated; wherein the electrode includes a motor for varying the electrode position to prevent formation of microdischarges in the plasma induced by the system during system operation; and
b) a power supply in electrical communication with the electrode, the power supply being configured to apply a pulsed voltage waveform having pulses with durations between about one picosecond and about 100 nanoseconds to help prevent formation of microdischarges between the electrode and the anatomical region of interest.

2. The system of claim 1, further comprising a control system operably coupled to the power supply and the electrode, the control system being operably coupled to at least one sensor that is configured to detect an operational condition of the power supply, the electrode, or the plasma, the control system being configured to perform closed loop control of an exposure dose and intensity of the plasma in response to an input from the at least one sensor.

3. The system of claim 2, wherein the at least one sensor includes an optical sensor that is configured to detect visible, ultraviolet, or infrared emissions from the plasma generated by the system.

4. The system of claim 2, wherein the at least one sensor includes an electrical sensor that is configured to detect electrical current flow through the system.

5. The system of claim 2, wherein the at least one sensor includes an electrical sensor that is configured to detect electrical field variation generated by the plasma emission.

6. The system of claim 1, wherein the system further includes at least one grounding pad configured to be attached to a patient operably coupled to the system for reducing current density delivered to the anatomical region of interest to be treated with the plasma.

7. The system of claim 6, wherein the at least one grounding pad includes an active cooling mechanism to prevent excessive heat from being delivered to the anatomical region of interest to be treated with the plasma.

8. The system of claim 6, wherein the system includes two grounding pads that cooperate to define a conductive pathway through the anatomical region of interest to be treated with the plasma in cooperation with the power supply and a control system, and further wherein the system is configured to direct a test current through the two grounding pads and the anatomical region of interest to be treated with the plasma and to monitor an impedance of a circuit to determine if the two grounding pads are not fully attached to the anatomical region of interest to be treated with the plasma.

9. The system of claim 1, wherein the system includes a fluid dispenser for controllably releasing fluid toward the anatomical region of interest to be treated with the plasma.

10. The system of claim 9, wherein the fluid includes at least one of a water based cream, an ointment, a lotion, a spray, and a gel.

11. The system of claim 9, wherein the fluid includes glycerin.

12. The system of claim 1, wherein the electrode includes a flexible plasma emitter that is configured to be inflated by directing fluid into a reservoir in the flexible plasma emitter.

13. The system of claim 12, wherein the flexible plasma emitter is configured to match the anatomical region to be treated with plasma.

14. The system of claim 12, wherein the electrode includes electrodes encapsulated in an insulation layer, and wherein the insulation layer defines thereon a plurality of spacers defining gaps therebetween for the formation of plasma on the surface of the flexible plasma emitter.

15. The system of claim 12, wherein the flexible plasma emitter defines a plurality of openings therethrough in fluid communication with the reservoir, and wherein a working gas is directed through the openings to the outer surface of the device to facilitate plasma generation.

16. The system of claim 1, wherein the motor is an oscillatory motor.

17. The system of claim 1, wherein the motor is a piezo-motor.

18. A system for applying a plasma discharge, comprising:
a) an electrode adapted to be placed proximate an anatomical region of interest, wherein the electrode includes a motor for varying the electrode position to facilitate uniformity in exposure to the anatomical region of interest exposed to the plasma discharge induced by the system during system operation; wherein the electrode is defined at least in part by a flexible electrode surface that is configured to conform to the curvature of the anatomical region of interest to be treated with the plasma discharge to create a substantially uniform gap between the flexible electrode surface and the anatomical region of interest to be treated to facilitate formation of a substantially uniform plasma across the anatomical region to be treated; and
b) a power supply in electrical communication with the electrode, the power supply being configured to apply a pulsed voltage waveform having pulses with durations between about 0.010 seconds and about 0.0000010 seconds to help prevent formation of microdischarges between the electrode and the anatomical region of interest in cooperation with movement of the motor.

19. The system of claim 18, further comprising a control system operably coupled to the power supply and the electrode, the control system being operably coupled to at least one sensor that is configured to detect an operational condition of the power supply, electrode, or plasma, the control system being configured to perform closed loop control of the exposure dose and intensity of the plasma in response to input from the at least one sensor.

20. The system of claim 19, wherein the at least one sensor includes an optical sensor that is configured to detect visible, ultraviolet, or infrared emissions from the plasma generated by the system.

21. The system of claim 19, wherein the at least one sensor includes an electrical sensor that is configured to detect electrical current flow through the system.

22. The system of claim 19, wherein the at least one sensor includes an electrical sensor that is configured to detect electrical field variation generated by the plasma emission.

23. The system of claim 19, wherein the system further includes at least one grounding pad configured to be attached to a patient operably coupled to the system for reducing current density delivered to the anatomical region to be treated with plasma.

24. The system of claim 18, wherein the motor is an oscillatory motor.

25. The system of claim 18, wherein the motor is a piezo-motor.

* * * * *